United States Patent
Jiang et al.

(10) Patent No.: US 9,890,181 B2
(45) Date of Patent: Feb. 13, 2018

(54) SILICON PHTHALOCYANINE COMPLEX, PREPARATION METHOD AND MEDICINAL APPLICATION THEREOF

(71) Applicant: Shenzhen China Resources Gosun Pharmaceutical Co., Ltd., Shenzhen (CN)

(72) Inventors: Xiongjie Jiang, Shenzhen (CN); Quanhua Huang, Shenzhen (CN); Zhanao Yang, Shenzhen (CN)

(73) Assignee: Shenzhen China Resources Gosun Pharmaceutical Co., Ltd., Shenzhen, Guangdong (CN)

( * ) Notice: Subject to any disclaimer, the term of this patent is extended or adjusted under 35 U.S.C. 154(b) by 90 days.

(21) Appl. No.: 14/974,747

(22) Filed: Dec. 18, 2015

(65) Prior Publication Data

US 2017/0002028 A1    Jan. 5, 2017

(30) Foreign Application Priority Data

Jun. 30, 2015  (CN) .......................... 2015 1 0385988

(51) Int. Cl.
  *C07F 7/02*    (2006.01)
  *C07D 487/22*  (2006.01)
  *A61K 41/00*   (2006.01)

(52) U.S. Cl.
  CPC .......... *C07F 7/025* (2013.01); *A61K 41/0057* (2013.01); *C07D 487/22* (2013.01)

(58) Field of Classification Search
  CPC .... C07F 7/025; C07D 487/22; A61K 41/0057
  See application file for complete search history.

(56) References Cited

U.S. PATENT DOCUMENTS 4,917,989 A * 4/1990 Albert .................... G11B 7/246
                                                346/135.1
5,484,778 A   1/1996 Kenney et al.

FOREIGN PATENT DOCUMENTS

| CN | 1583762   | 2/2005  |
| CN | 1861603   | 11/2006 |
| CN | 104177393 | 12/2014 |
| CN | 104230944 | 12/2014 |

OTHER PUBLICATIONS

Biyiklioğlu et al. "Novel axially disubstituted non-aggregated silicon phthalocyanines" Spectrochimica Acta Part A: Molecular and Biomolecular Spectroscopy, 2012, vol. 98, pp. 178-182.*
"European Application No. 15197868.1, Extended European Search Report dated Nov. 2, 2016", (Nov. 2, 2016), 8 pgs.
"International Application No. PCT/CN2015/088596, International Search Report and Written Opinion dated Apr. 5, 2016", (Apr. 5, 2016), 7 pgs.
Jiang, Xiong-Jie, et al., "Phthalocyanin-Polyamine Conjugates as Highly Efficient Photosensitizers for Photodynamic Therapy", J Med Chem 2011, 54, 320-330, (2011), 320-330.
Lau, Janet T.F., et al., "Preparation and Photodynamic Activities of Silicon(IV) Phthalocyanines Substituted with Permethylated b-Cyclodextrins", Chem. Eur. J. 2011, 17, 7569-7577, (2011), 7569-7577.

* cited by examiner

*Primary Examiner* — Joseph R Kosack
(74) *Attorney, Agent, or Firm* — Schwegman Lundberg & Woessner, P.A.

(57) ABSTRACT

The present invention relates to a silicon phthalocyanine complex, the preparation method and the medicinal application thereof. The present invention particularly relates to a silicon phthalocyanine complex of formula (I), the preparation method thereof and a pharmaceutical composition comprising the same, as well as the use thereof as a photosensitizer, in particular the use in the treatment of cancers, wherein each substituent in formula (I) is the same as defined in the description.

13 Claims, No Drawings

SILICON PHTHALOCYANINE COMPLEX, PREPARATION METHOD AND MEDICINAL APPLICATION THEREOF

CLAIM OF PRIORITY

This application claims the benefit of priority of China Patent Application No. 201510385988.2, filed on 30 Jun. 2015, the benefit of priority of which is claimed hereby, and which is incorporated by reference herein in its entirety.

FIELD OF THE INVENTION

The present invention belongs to the field of medicine and relates to a silicon phthalocyanine complex, the preparation method and the medicinal application, and discloses the use of the complex as a photosensitizer for the treatment of cancers.

BACKGROUND OF THE INVENTION

Photodynamic therapy (abbreviated as PDT), also known as photoradiation therapy (abbreviated as PRT) or also known as photochemotherapy, is a treatment method on the basis of the photochemical reaction principle of specific chemical substances. The chemical substance used therein is referred to as a chemical diagnosis and treatment drug for tumor (also known as a photosensitizer, abbreviated as PS). The PDT process lies in that a photosensitizer is intravenously injected into the body (for the skin, it can also be applied to the affected area), and after a certain time the tumor tissue is irradiated with a specific wavelength of light, the photosensitizer enriched in the tumor tissue under the excitation of light generates a series of photophysical chemical reactions and generates cytotoxic reactive oxygen species, thereby killing the cancer cells to destroy the tumor tissue.

This therapy was approved by the US FDA for clinical use in 1996, and listed as one of the five basic methods for tumor treatment (surgery, radiotherapy, chemotherapy, photodynamic therapy, biochemical immunology) by FDA in 1997. Compared with traditional therapies, the PDT has the advantages of small trauma, low toxicity, good selectivity, good applicability, repeatable treatment, palliative treatment, and can be combined with a surgery to improve the efficacy, can eliminate the occult cancerous lesions, can protect the appearance and vital organ function, and the treatment time is short, etc.

The photodynamic therapy may also be effective in treating non-cancer diseases such as bacterial infections, oral infections, eye diseases of macular degeneration, atherosclerosis, wound infections, and skin diseases etc. The photosensitizer can also be used for photodynamic disinfection, most importantly for the sterilization and disinfection of blood and blood derivatives. Meanwhile, the fluorescence property of the photosensitizer can be used for photodynamic diagnosis, which is also an important use of the medical photosensitizer.

Photosensitizer is the key of the photodynamic therapy and the photodynamic effect depends on the good or bad photosensitizer. Based on the potential of the photodynamic therapy in the treatment of cancers and other diseases, it is generally believed in the scientific field that the photodynamic therapy will become an important method of medical treatment in the 21st century. The main clinical photosensitizer used currently is porfimer sodium, the first generation of photosensitizer. In 1993, Photofrin II is officially put into production by Quadra Logic Technologies Phototherapeutics Inc (Canadian), and the trade name is porfimer sodium. The drug went on sale in Netherland (1994), Canada (1995), Japan (1996), United States (1996), France (1997), Germany (1997), the United Kingdom (2001), Israel (2002), Portugal (2002), Greece (2003) and the like successively.

Although porfimer sodium achieved clinical success, but its components are complicated, the effects of various components in photodynamic injury have also not been made clear; the inactive ingredients accounting for more than 20% of the total drug not only failed to produce effective photodynamic injury to the lesion target tissue but became a culprit resulting in photosensitivity reactions in normal tissues. Therefore, the tissue selectivity and stability of the photodynamic damage strength of first generation of photosensitizers are very poor, the skin phototoxicity is strong, and the time away from light is long (after the treatment, the patients must be strictly protected from light for 4-6 weeks). In addition, there is a very weak absorption band in the absorption spectrum of a mixed porphyrin photosensitizer at the treatment wavelength of 630 nm, such a photosensitizer cannot absorb the red light part well, and the treatment depth is not enough (about 2 mm), which also affects its clinical efficacy. Although these deficiencies did not prevent porfimer sodium from becoming a useful drug for anti-cancers and other diseases, the exploration of the second generation of photosensitizer having better physical, chemical and spectral properties becomes more meaningful.

The phthalocyanine complex as a photosensitizer in the PDT treatment is better than porfimer sodium in clinical use, and its advantages can be summarized as follows: 1) its structure is clear, and its properties are stable. It has a large conjugated system, a clear structure, and stable properties. Also, the central ion, axial ligands, type and number of substituents on the rings can be changed as required to synthesize a desired drug, and there are great alternatives; 2) the preparation is relatively easy, and the cost is lower; 3) there is an optimal effect wavelength and stronger penetration to the tissue. The phthalocyanine complex generally has a maximum absorption wavelength of between 660-700 nm, its absorption to the light of a wavelength of 680 nm is 10-50 times stronger than porfimer sodium, and the ability to penetrate the skin tissue of the 680 nm light increased by 20% than that of the 630 nm light, and the ability to penetrate brain tissue increased by 50%, so the phthalocyanine complex is more suitable for the treatment of deep tissue cancers than porfimer sodium; 4) the dark toxicity is low, and the skin phototoxicity is low. Although there are many phthalocyanine complexes which have been studied as photosensitizers, there are no phthalocyanine photosensitizers saled in the market. Therefore, the second generation of phthalocyanine photosensitive drug having high activity and low toxicity is the recent research focus.

SUMMARY OF THE INVENTION

The object of the present invention lies in a compound of formula (I):

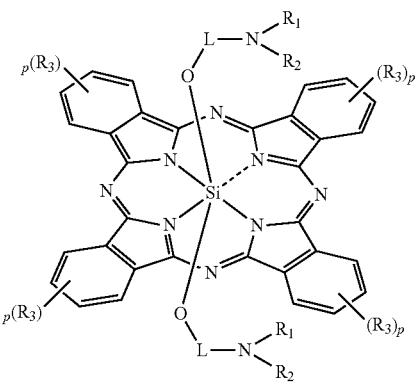

(I)

or a tautomer, mesomer, racemate, enantiomer, diastereoisomer thereof, or mixture thereof, or a pharmaceutically acceptable salt thereof, wherein:

L is selected from the group consisting of —CH$_2$—CH$_2$—O—CH$_2$—CH$_2$—, —CH$_2$—CH$_2$—O—CH$_2$—CH$_2$—O—CH$_2$—CH$_2$— and —CH$_2$—CH$_2$—CH$_2$—, wherein one or more hydrogens are optionally substituted by a group selected from the group consisting of C$_{1-4}$alkyl, haloC$_{1-4}$alkyl, C$_{1-4}$alkoxy, haloC$_{1-4}$alkoxy, halo, amino, nitro, hydroxyl and cyano;

R$_1$ and R$_2$ are each independently selected from the group consisting of a hydrogen atom, C$_{1-4}$alkyl, —C$_{1-4}$alkylene-O—C$_{1-4}$alkyl, —C$_{1-4}$alkylene O—C$_{1-4}$alkylene-O—C$_{1-4}$alkyl and —C$_{1-4}$alkylene-O—C$_{1-4}$alkylene-O—C$_{1-4}$alkylene-O—C$_{1-4}$alkyl, wherein said C$_{1-4}$alkyl and C$_{1-4}$alkylene are optionally substituted by one or more groups selected from the group consisting of C$_{1-4}$alkyl, haloC$_{1-4}$alkyl, C$_{1-4}$alkoxy, haloC$_{1-4}$alkoxy, halo, amino, nitro, hydroxyl and cyano; or R$_1$ and R$_2$ together with the atoms to which they are attached form a following group:

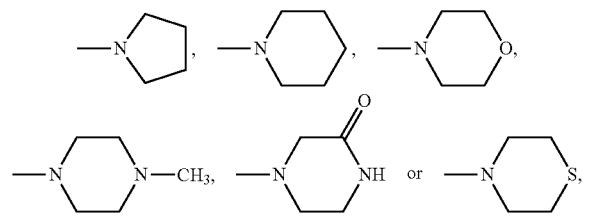

said group is optionally substituted by one or more groups selected from the group consisting of C$_{1-4}$alkyl, haloC$_{1-4}$alkyl, C$_{1-4}$alkoxy, haloC$_{1-4}$alkoxy, halogen, amino, nitro, hydroxyl and cyano;

R$_3$ are the same or different and are each independently selected from the group consisting of a hydrogen atom, C$_{1-4}$alkyl, haloC$_{1-4}$alkyl, C$_{1-4}$alkoxy, haloC$_{1-4}$alkoxy, halogen, amino, nitro, hydroxyl and cyano groups, and p is an integer of 0, 1, 2, 3 or 4;

on the condition that when L is —CH$_2$—CH$_2$—CH$_2$—, R$_1$ and R$_2$ together with the atoms to which they are attached do not form

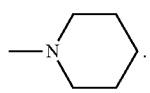

In a preferred embodiment of the present invention, R$_1$ and R$_2$ are each independently selected from the group consisting of a hydrogen atom, methyl, ethyl, —CH$_2$—CH$_2$—O—CH$_3$, —CH$_2$—CH$_2$—CH$_2$—O—CH$_3$, —CH$_2$—CH$_2$—O—CH$_2$—CH$_2$—O—CH$_3$ and —CH$_2$—CH$_2$—O—CH$_2$—CH$_2$—O—CH$_2$—CH$_2$—O—CH$_3$.

In another preferred embodiment of the present invention, R$_3$ is a hydrogen atom.

In another preferred embodiment of the present invention, p is 0.

In another preferred embodiment of the present invention:

L is —CH$_2$—CH$_2$—O—CH$_2$—CH$_2$—; and

R$_1$ and R$_2$ are each independently selected from the group consisting of a hydrogen atom, C$_{1-4}$alkyl, —CH$_2$—CH$_2$—O—CH$_3$ and —CH$_2$—CH$_2$—CH$_2$—O—CH$_3$; or R$_1$ and R$_2$ together with the atoms to which they are attached form a following group:

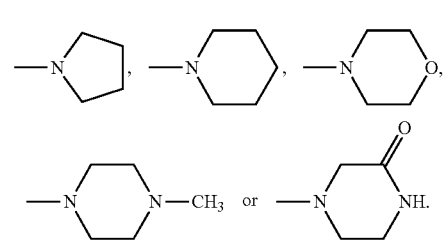

In another preferred embodiment of the present invention:

L is —CH$_2$—CH$_2$—O—CH$_2$—CH$_2$—O—CH$_2$—CH$_2$—; and

R$_1$ and R$_2$ are each independently selected from the group consisting of a hydrogen atom, C$_{1-4}$alkyl, —CH$_2$—CH$_2$—O—CH$_3$ and —CH$_2$—CH$_2$—CH$_2$—O—CH$_3$; or R$_1$ and R$_2$ together with the atoms to which they are attached form a following group:

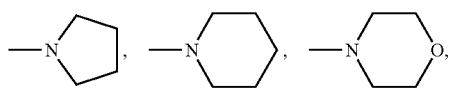

In another preferred embodiment of the present invention:

L is —CH$_2$—CH$_2$—CH$_2$—;

R$_1$ is a hydrogen atom; and

R$_2$ is selected from the group consisting of —CH$_2$—CH$_2$—O—CH$_3$, —CH$_2$—CH$_2$—O—CH$_2$—CH$_2$—O—CH$_3$ and —CH$_2$—CH$_2$—O—CH$_2$—CH$_2$—O—CH$_2$—CH$_2$—O—CH$_3$.

Typical compounds of the present invention include, but are not limited to:

| Compound No. | Structure and Name |
|---|---|
| 1 | 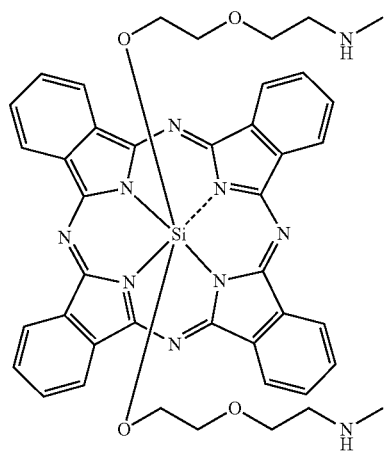<br>bis{2-[2-(methylamino)ethoxy]ethoxy}silicon(IV) phthalocyanine |
| 2 | 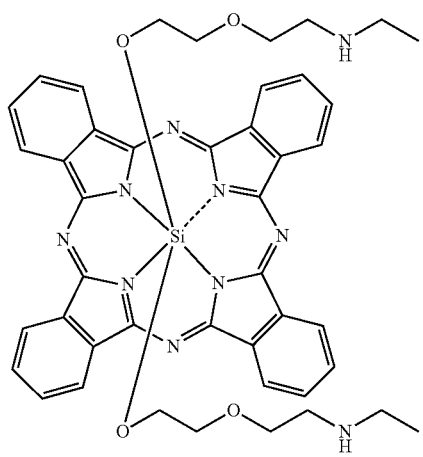<br>bis{2-[2-(ethylamino)ethoxy]ethoxy}silicon(IV) phthalocyanine |
| 3 | 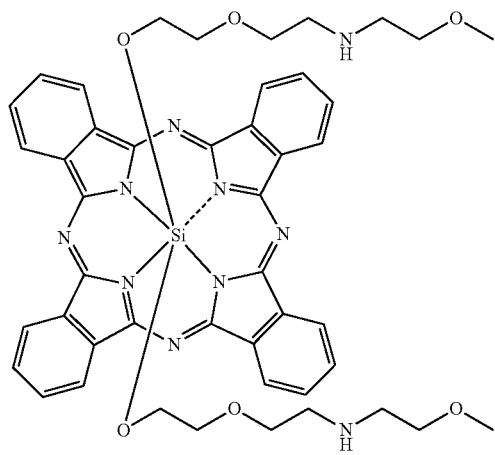<br>bis{2-[2-(2-methoxyethylamino)ethoxy]ethoxy}silicon(IV) phthalocyanine |

-continued
| Compound No. | Structure and Name |
|---|---|
| 4 | 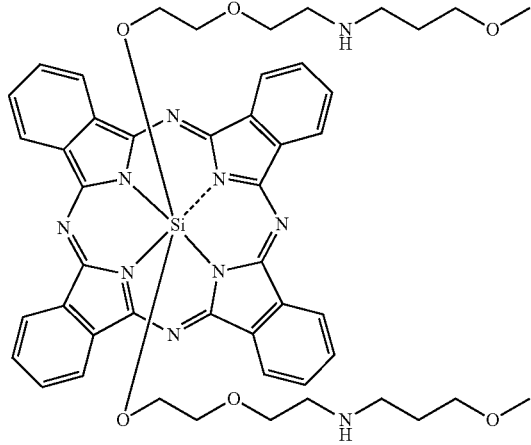<br>bis{2-[2-(2-methoxypropylamino)ethoxy]ethoxy}silicon(IV) phthalocyanine |
| 5 | 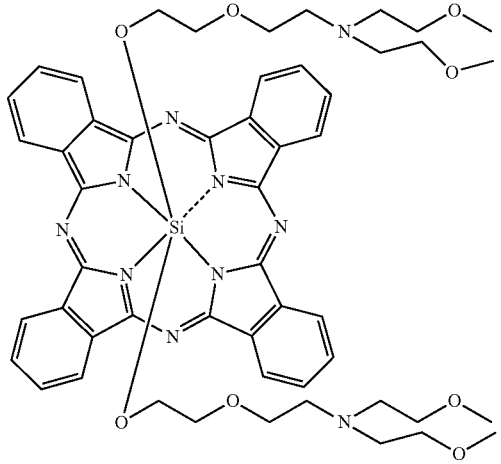<br>bis{2-{2-[bis(2-methoxyethyl)amino]ethoxy}ethoxy}silicon(IV) phthalocyanine |
| 6 | 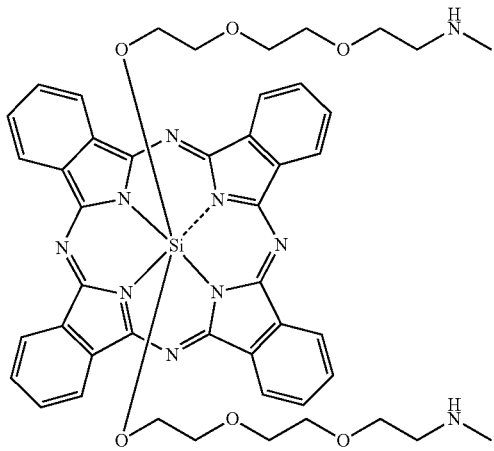<br>bis{2-{2-[2-(methylamino)ethoxy]ethoxy}ethoxy}silicon(IV) phthalocyanine |

-continued

| Compound No. | Structure and Name |
|---|---|
| 7 | bis{2-{2-[2-(ethylamino)ethoxy]ethoxy}ethoxy}silicon(IV) phthalocyanine |
| 8 | bis{2-{2-[2-(2-methoxyethylamino)ethoxy]ethoxy}ethoxy} silicon(IV) phthalocyanine |
| 9 | bis{2-{2-[2-(2-methoxypropylamino)ethoxy]ethoxy}ethoxy}silicon(IV) phthalocyanine |

-continued
| Compound No. | Structure and Name |
|---|---|
| 10 | 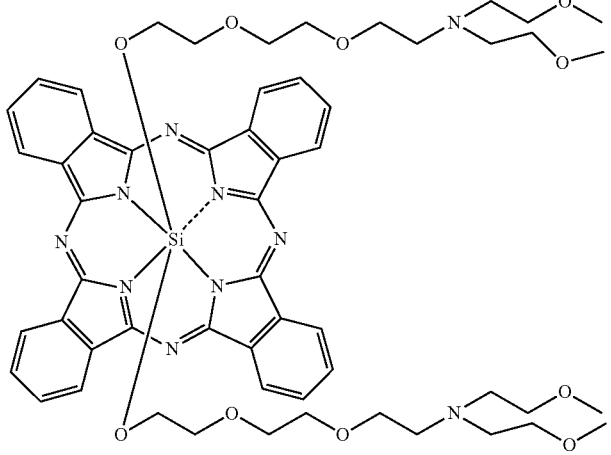<br>bis{2-{2-{2-[bis(2-methoxyethyl)amino]ethoxy}ethoxy}ethoxy} silicon(IV) phthalocyanine |
| 11 | 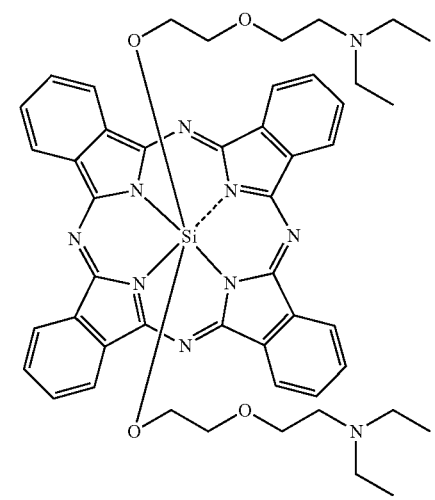<br>bis{2-[2-(diethylamino)ethoxy]ethoxy}silicon(IV) phthalocyanine |
| 12 | 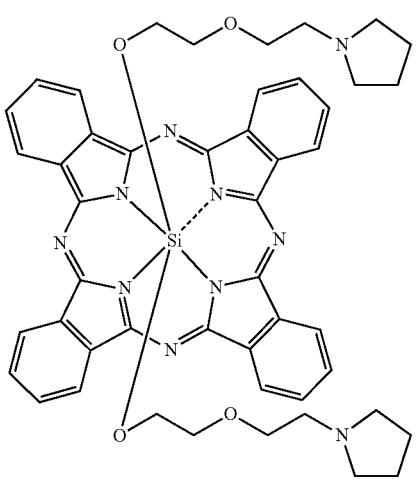<br>bis{2-[2-(1-pyrrolidinyl)ethoxy]ethoxy}silicon(IV) phthalocyanine |

| Compound No. | Structure and Name |
|---|---|
| 13 | 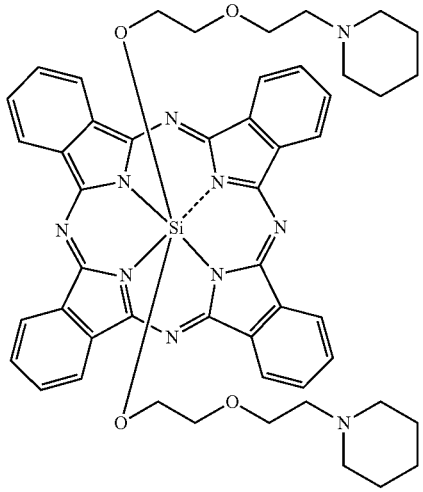<br>bis{2-[2-(1-piperidinyl)ethoxy]ethoxy}silicon(IV) phthalocyanine |
| 14 | 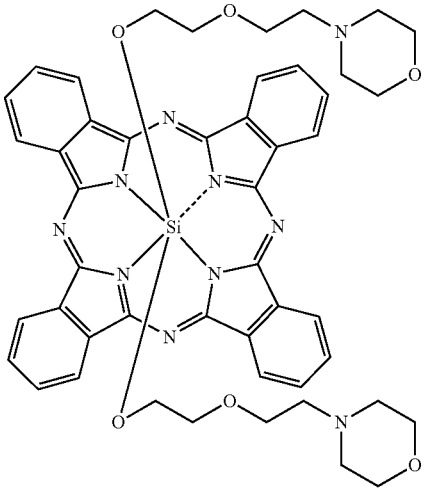<br>bis[2-(2-morpholinylethoxy)ethoxy]silicon(IV) phthalocyanine |

-continued
| Compound No. | Structure and Name |
|---|---|
| 15 | 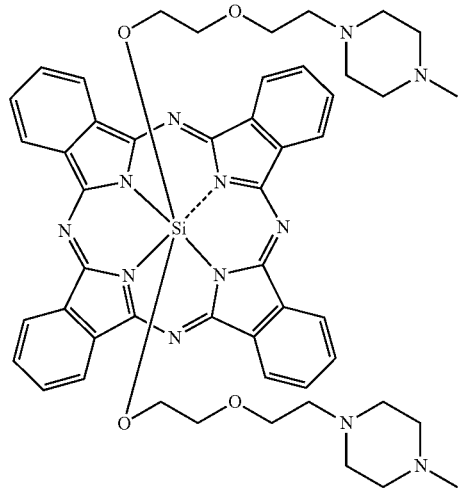  bis{2-[2-(4-methyl-1-piperazinyl)ethoxy]ethoxy}silicon(IV) phthalocyanine |
| 16 | 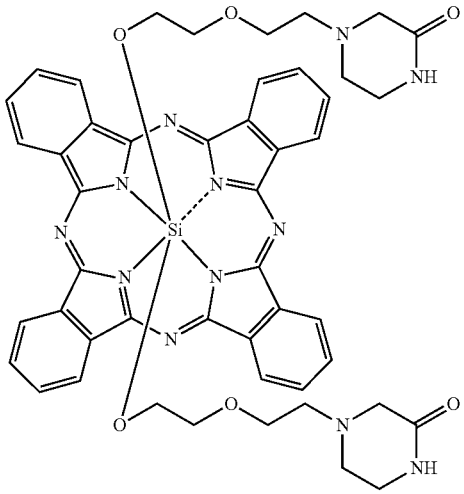  bis{2-[2-(1-piperazinyl-3-one)ethoxy]ethoxy}silicon(IV) phthalocyanine |

| Compound No. | Structure and Name |
|---|---|
| 17 | 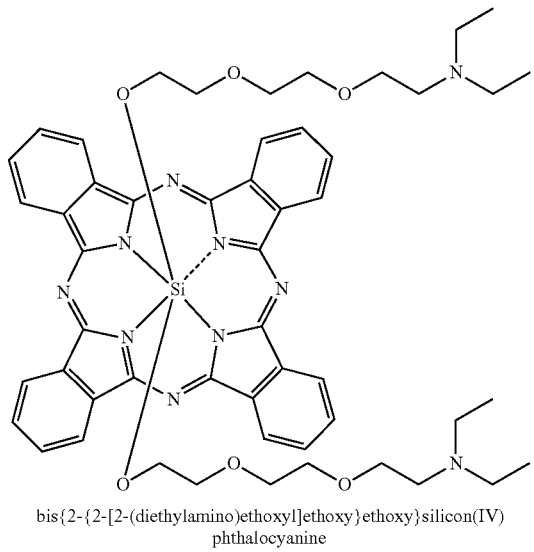<br>bis{2-{2-[2-(diethylamino)ethoxyl]ethoxy}ethoxy}silicon(IV) phthalocyanine |
| 18 | 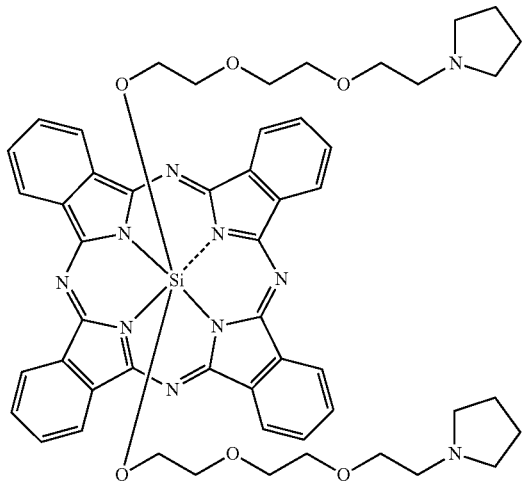<br>bis{2-{2-[2-(1-pyrrolidinyl)ethoxy]ethoxy}ethoxy}silicon(IV) phthalocyanine |

-continued
| Compound No. | Structure and Name |
|---|---|
| 19 | 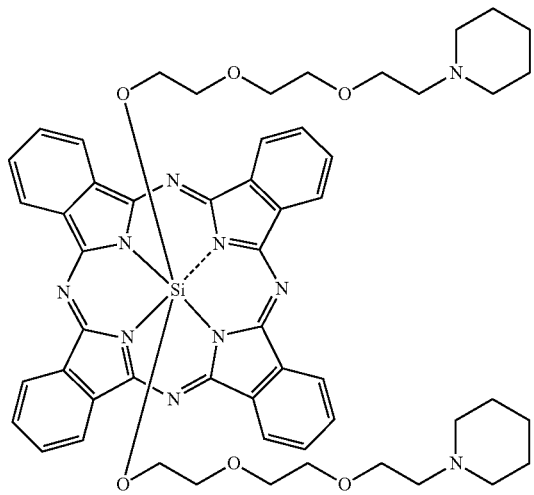<br>bis{2-{2-[2-(1-pyrrolidinyl)ethoxy]ethoxy}ethoxy}silicon(IV) phthalocyanine |
| 20 | 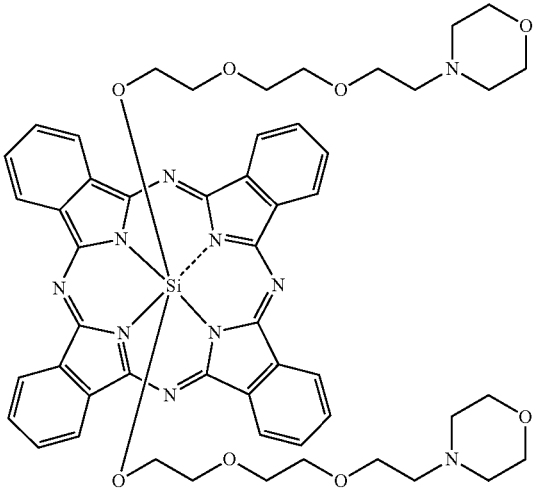<br>bis{2-{2-[2-(1-morpholinyl)ethoxy]ethoxy}ethoxy}silicon(IV) phthalocyanine |

-continued
| Compound No. | Structure and Name |
|---|---|
| 21 | 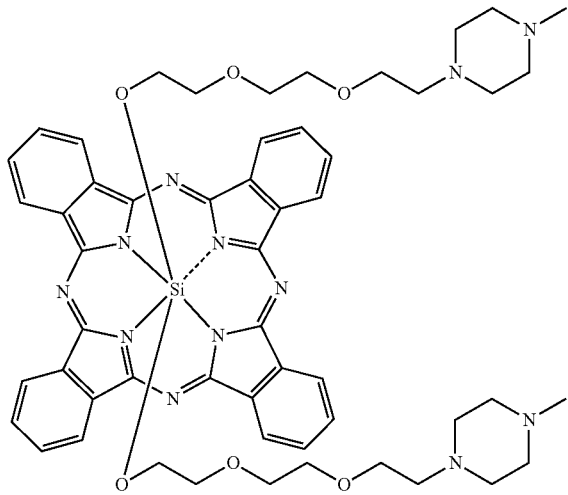bis{2-{2-[2-(4-methyl-1-piperazinyl)ethoxy]ethoxy}ethoxy}silicon (IV) phthalocyanine |
| 22 | 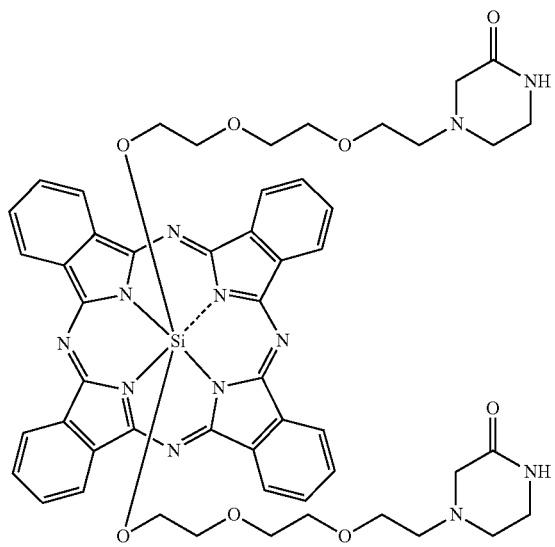bis{2-{2-[2-(1-piperazinyl-3-one)ethoxy]ethoxy}ethoxy}silicon(IV) phthalocyanine |

-continued
| Compound No. | Structure and Name |
|---|---|
| 23 | 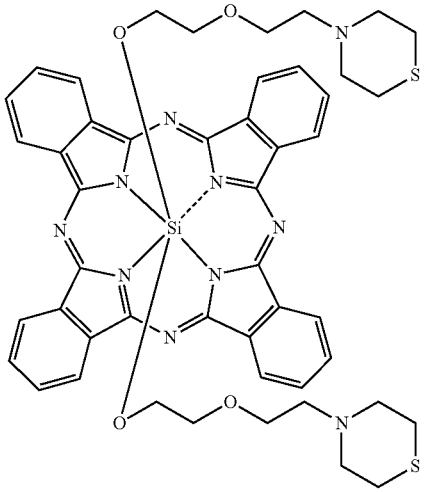
bis[2-(2-thiomorpholinylethoxy)ethoxy]silicon(IV) phthalocyanine |
| 24 | 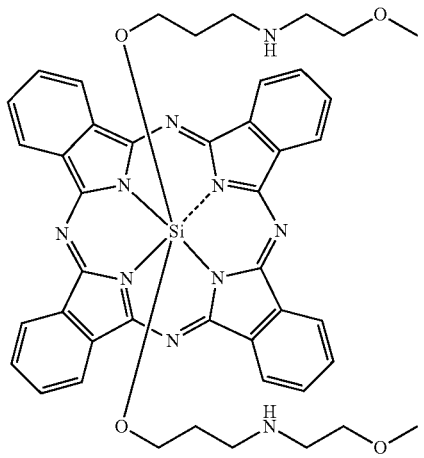
bis[3-(2-methoxyethylamino)propoxy]silicon(IV) phthalocyanine |
| 25 | 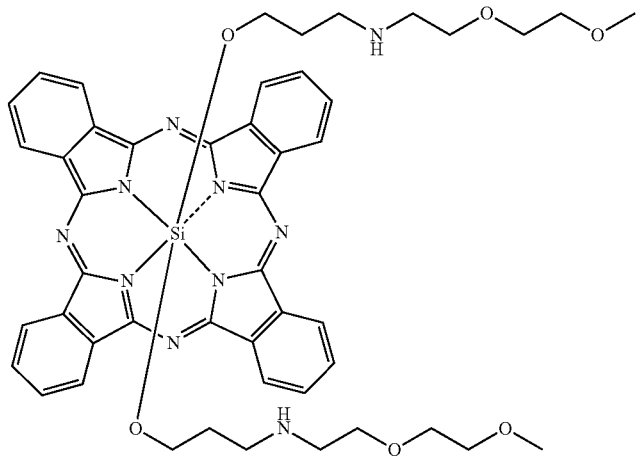
bis{3-[2-(2-methoxyethoxy)ethylamino]propoxy}silicon(IV) phthalocyanine |

| Compound No. | Structure and Name |
|---|---|
| 26 | 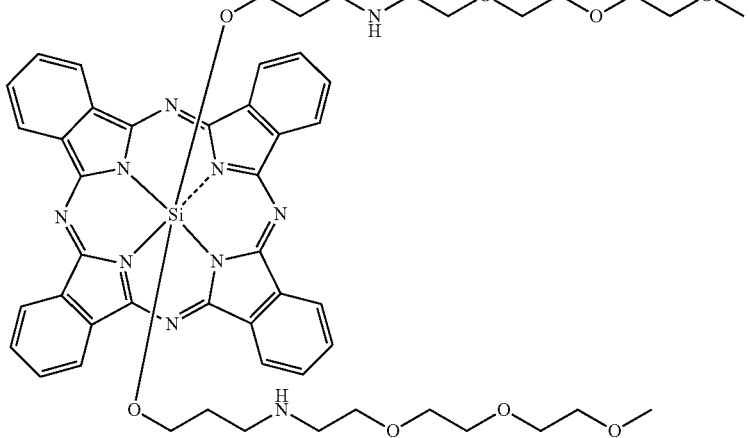<br>bis{3-{2-[2-(2-methoxyethoxy)ethoxy]ethylamino}propoxy}silicon (IV) phthalocyanine | or a tautomer, mesomer, racemate, enantiomer, diastereoisomer thereof, or mixture thereof, or a pharmaceutically acceptable salt thereof.

The invention also relates to a process for the preparation of the compound of formula (I), comprising:

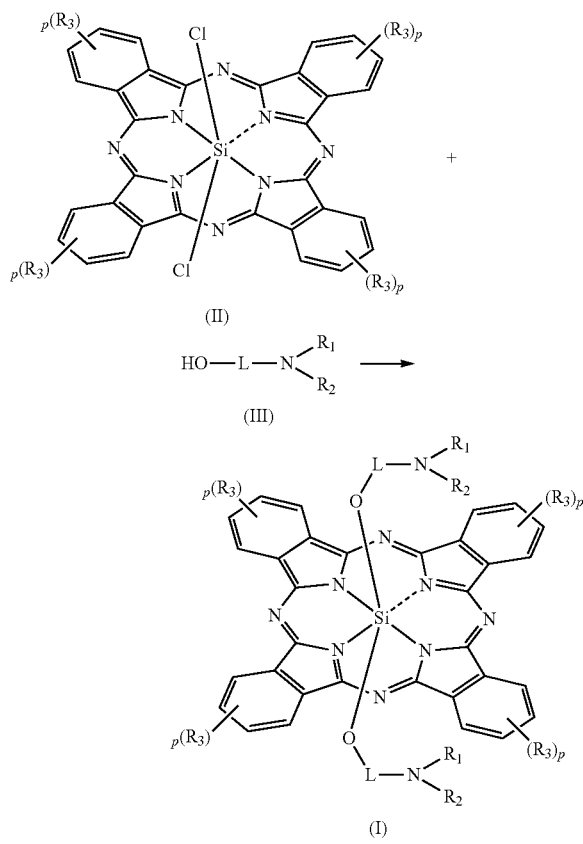

reacting a compound of formula (II) with a compound of formula (III) in an organic solvent under alkaline condition to obtain the compound of formula (I);

wherein L, $R_1$-$R_3$ and p are as defined in formula (I).

In another preferred embodiment of the present invention:

the molar ratio of the compound of formula (II) to the compound of formula (III) is 1:1-4, preferably 1:2-3;

said organic solvent is selected from the group consisting of toluene, benzene, xylene, hexane, N,N-dimethylformamide, dimethylsulfoxide, ethyl acetate and acetone, preferably toluene;

said alkaline condition are provided by a reagent selected from the group consisting of pyridine, sodium hydride, triethylamine, N,N-diisopropylethylamine, 4-dimethylaminopyridine, potassium carbonate and sodium carbonate, preferably from pyridine or sodium hydride;

said reaction is carried out at a temperature of 0-200° C., preferably 20° C.-140° C.

If necessary, the compound can also be purified by well-known methods by those skilled in the art, for example, by distillation, by silica gel column chromatography or by high performance liquid chromatography (HPLC).

The present invention also provides a pharmaceutical composition, comprising a therapeutically effective amount of a compound of formula (I) or a tautomer, mesomer, racemate, enantiomer, diastereoisomer thereof, or mixture thereof, or a pharmaceutically acceptable salt thereof, and a pharmaceutically acceptable carrier, diluent or excipient.

The present invention also relates to the use of the compound of formula (I) or a tautomer, mesomer, racemate, enantiomer, diastereoisomer thereof, or mixture thereof, or a pharmaceutically acceptable salt thereof or the pharmaceutical composition comprising the same in the preparation of a photodynamic medicament or a photosensitive medicament.

The present invention also relates to the use of the compound of formula (I) or a tautomer, mesomer, racemate, enantiomer, diastereoisomer thereof, or mixture thereof, or a pharmaceutically acceptable salt thereof or the pharmaceutical composition comprising the same in the preparation of a medicament for treating cancers. The cancers described herein are selected from the group consisting of skin cancer, esophageal cancer, lung cancer, brain tumor, head and neck cancer, eye tumor, inflammatory carcinoma, breast cancer, bladder cancer, rectal cancer, liver cancer, bile duct cancer, stomach cancer and ovarian cancer, preferably skin cancer and esophageal cancer.

The present invention also relates to the compound of formula (I) or a tautomer, mesomer, racemate, enantiomer, diastereoisomer thereof, or mixture thereof, or a pharmaceutically acceptable salt thereof or the pharmaceutical composition comprising the same, for use as a photodynamic medicament or a photosensitive medicament.

The present invention also relates to the compound of formula (I) or a tautomer, mesomer, racemate, enantiomer, diastereoisomer thereof, or mixture thereof, or a pharmaceutically acceptable salt thereof or the pharmaceutical composition comprising the same, for use in treating cancers. The cancers described herein are selected from the group consisting of skin cancer, esophageal cancer, lung cancer, brain tumor, head and neck cancer, eye tumor, inflammatory carcinoma, breast cancer, bladder cancer, rectal cancer, liver cancer, bile duct cancer, stomach cancer and ovarian cancer, preferably skin cancer and esophageal cancer.

The present invention also relates to a method of treating cancers, comprising the steps of administering to a patient in need thereof a therapeutically effective amount of the compound of formula (I) or a tautomer, mesomer, racemate, enantiomer, diastereoisomer thereof, or mixture thereof, or a pharmaceutically acceptable salt thereof or the pharmaceutical composition comprising the same, and then irradiating the patient with a suitable light source. Said suitable light source may be provided by a common light source connected to a suitable filter or provided by a specific wavelength of laser light, and the wavelength range of the light source is 600-800 nm, preferably 610-690 nm.

The compounds according to the present invention can be administrated by orally, sublingually, parenterally, subcutaneously, intramuscularly, intravenously, transdermally, locally or rectally.

In the pharmaceutical compounds of the present invention, for oral, sublingual, parenteral, subcutaneous, intramuscular, intravenous, transdermal, local or rectal administration, the active ingredient may be mixed together with a conventional pharmaceutically acceptable carrier, and be administered in unit forms of administration to animals or humans beings. Suitable unit forms of administration include oral forms such as tablets, gel capsules, powders, granules and oral solutions or suspensions, sublingual or buccal forms of administration, parenteral, subcutaneous, intramuscular, intravenous, intranasal or intraocular forms of administration and rectal forms of administration.

When a solid composition is prepared in the form of tablets, the principal active ingredient is mixed with a pharmaceutical carrier such as gelatin, starch, lactose, magnesium stearate, talc, gum arabic or the like. The tablets may be coated with sucrose or other suitable materials or else treated in such a way that they have an extended or delayed activity and continuously release a predetermined amount of active principle.

A gel capsule preparation can be obtained by mixing the active ingredient with a diluent and by pouring the mixture obtained into soft or hard capsules.

A preparation in the form of a syrup or elixir may contain the active ingredient in conjunction with a sweetening agent, antiseptic, as well as a flavour-producing agent and appropriate colouring agent.

Powders or granules dispersible in water can contain the active ingredient mixed together with dispersing agents, wetting agents, or suspending agents, as well as with taste correctors or sweetening agents.

For rectal administration, suppositories are used, which are prepared with binding agents melting at rectal temperature, e.g., cocoa butter or polyethylene glycols.

For parenteral, intranasal or intraocular administration, aqueous suspensions are used, isotonic saline solutions or sterile and injectable solutions, which contain pharmacologically compatible dispersing agents and/or wetting agents.

The active principle can also be formulated as microcapsules, possibly with one or more additive carriers.

The compounds of the present invention can be used at doses of between 0.01 mg and 1000 mg per day, given in a single dose once a day or administered in several doses throughout the day, e.g., twice daily in equal doses. The daily dose administered is advantageously between 0.1 mg and 100 mg, even more advantageously between 2.5 mg and 50 mg. It may be necessary to use doses exceeding these ranges, of which those skilled in the art will themselves be aware.

In one particular embodiment of the present invention, the pharmaceutical compositions can also be formulated for topical administration. It can be introduced in forms commonly known for this type of administration, i.e., especially lotions, foams, gels, dispersants, sprays, with excipients enabling, in particular, penetration of the skin so as to improve the properties and accessibility of the active principle. Besides the composition according to the invention, these compositions typically further contain a physiologically acceptable medium, which generally contains water or a solvent, e.g., an alcohol, an ether or ethylene glycol. Said compositions may also contain surfactants, preservatives, stabilizers, emulsifiers, thickeners, other active ingredients producing a complementary effect or a possibly synergistic effect, trace elements, essential oils, perfumes, colouring agents, collagen, chemical or mineral filters.

Definitions

Unless otherwise stated, the terms used in the description and claims have the following meanings.

In the present invention, "pharmaceutically acceptable" is understood to mean what is useful in the preparation of a pharmaceutical or cosmetic composition which is generally safe, non-toxic, and neither biologically nor otherwise undesirable and which is acceptable for veterinary and human pharmaceutical use.

In the present invention, the "pharmaceutically acceptable salt" of a compound is understood to refer to salts, which are pharmaceutically acceptable, as defined herein, and which possess the desired pharmacological activity of the parent compound. Such salts include:

(1) acid addition salts formed with inorganic acids such as hydrochloric acid, hydrobromic acid, sulfuric acid, nitric acid, phosphoric acid and the like; or acid addition salts formed with organic acids such as acetic acid, benzenesulfonic acid, benzoic acid, camphorsulfonic acid, citric acid, ethylsulfonic acid, fumaric acid, glucoheptonic acid, gluconic acid, glutamic acid, glycolic acid, hydroxynaphtoic acid, 2-hydroxylethylsulfonic acid, lactic acid, maleic acid, malic acid, mandelic acid, methanesulfonic acid, muconic acid, 2-naphthalenesulfonic acid, propionic acid, salicylic acid, succinic acid, dibenzoyl-L-tartaric acid, tartaric acid, p-toluenesulfonic acid, trimethylacetic acid, trifluoroacetic acid and the like; and (2) salts formed when an acidic proton present in parent compound is either replaced by a metal ion, e.g., an alkali metal ion (e.g., $Na^+$, $K^+$ or $Li^+$), an alkaline earth metal ion (e.g. $Ca^{2+}$ or $Mg^{2+}$), or an aluminum ion; or coordinates with an organic base or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

In the present invention, "tautomer" is understood to refer to an isomer obtained by prototropy, i.e. migration of a hydrogen atom and change of localisation of a double bond. The different tautomers of a compound are generally inter-convertible and present in equilibrium in solution, in various proportions which may depend on the solvent used, on the temperature or on the pH.

In the present invention, "halogen" refers to an atom of fluorine, bromine, chlorine or iodine.

"$C_{1-4}$alkyl" refers to a saturated, linear or branched hydrocarbon chain comprising 1 to 4 carbon atoms. Representative examples include, but are not limited to methyl, ethyl, n-propyl, isopropyl, n-butyl, iso-butyl, sec-butyl, t-butyl groups.

"$C_{1-4}$alkylene" refers to a divalent hydrocarbon chain comprising 1 to 4 carbon atoms, and the representative examples include, but are not limited to $CH_2$—, —$CH_2$—$CH_2$—, —$CH_2$—$CH_2$—$CH_2$—, —$CH_2$—$CH_2$—$CH_2$—$CH_2$—, and the like.

"$C_{1-4}$alkoxy" refers to an —O—($C_{1-4}$alkyl) group, wherein the $C_{1-4}$alkyl is defined as above. Representative examples include, but are not limited to methoxy, ethoxy, propyloxy, butoxy and the like.

"Halo$C_{1-4}$alkyl" refers to a $C_{1-4}$alkyl group substituted by one or more halogens, wherein the $C_{1-4}$alkyl and halogen are as defined above.

"Halo$C_{1-4}$alkoxy" refers to a $C_{1-4}$alkoxy group substituted by one or more halogens, wherein the $C_{1-4}$alkoxy and halogen are as defined above.

"Hydroxyl" refers to an —OH group.

"Nitro" refers to —$NO_2$.

"Hydrogen" refers to —H.

"Amino" refers to —$NH_2$.

"Cyano" refers to —CN.

"Optional" or "optionally" refers to that the event or circumstance subsequently described may, but need not occur, and the description includes the instances in which the event or circumstance occur or does not occur. For example, "heterocyclic group optionally substituted by an alkyl" refers to the alkyl may be, but need not be present, and the description includes the cases of the heterocyclic group being substituted by an alkyl and the heterocyclic group being not substituted by an alkyl.

"Substituted" refers to one or more hydrogen atoms in the group, preferably at most 5, more preferably 1-3 hydrogen atoms, each independently substituted by a corresponding number of substituents. It goes without saying that the substituents exist in their only possible chemical positions. The person skilled in the art can determine the possible or impossible substitutions without paying excessive efforts by experiment or theory. For example, the combination of amino or hydroxy group having free hydrogen and carbon atoms having unsaturated bonds (such as olefinic) may be unstable.

"Pharmaceutical composition" refers to a mixture comprising one or more of the compounds as described herein or physiologically/pharmaceutically acceptable salts or prodrug thereof and other chemical components, such as a physiologically/pharmaceutically acceptable carrier and an excipient. The purpose of a pharmaceutical composition is to promote administration of a compound to an organism, which is conducive to the absorption of the active ingredient, thus displaying biological activity.

DETAILED DESCRIPTION OF THE INVENTION

By reading the following examples, the person skilled in the art will better understand the present invention. It is to be understood that the following examples merely serve to explain the present invention.

Experimental methods in the examples of the present invention, for which no specific conditions are indicated, will be carried out according to conventional conditions or recommended conditions of the raw materials and the product manufacturer. The experimental reagents for which no specific sources are indicated will be conventional reagents generally purchased from market.

Nuclear Magnetic Resonance Spectrometer: Bruker ARX-500 machine and Bruker ARX-400 machine.

Mass spectrometry: QSTAR Elite tandem quadrupole time-of-flight mass spectrometer.

MTT detecting instrument: Thermo Scientific Multiskan GO Multiskan Spectrum Microplate Reader The structures of the compounds are determined by nuclear magnetic resonance (NMR) and/or mass spectrometry (MS). NMR chemical shift ($\delta$) is given in $10^{-6}$ (ppm). The solvent for determination is deuterated chloroform ($CDCl_3$), and the internal standard is tetramethylsilane (TMS). The following abbreviations are used: s for singlet, bs for broad singlet, d for doublet, t for triplet, qdt for quartet, m for multiplet or massive, dd for double of doublet, etc.

Qingdao GF254 silica gel plate is used for thin layer chromatography (TLC) silica plate, and the dimension of the plates used in TLC is 0.15 mm-0.2 mm, and the dimension of the plates used in product purification is 0.4 mm-0.5 mm.

For the column chromatography, Yantai Huanghai silica gel of 200-300 mesh silica gel is generally used as a carrier.

If there is no special instruction in the examples, the reactions are carried out under an argon atmosphere or a nitrogen atmosphere.

If there is no special instruction in the examples, the reaction solution refers to an aqueous solution.

If there is no special instruction in the examples, the reaction temperature is room temperature.

The reaction progress in the examples is monitored by thin layer chromatography (TLC).

EXAMPLE 1

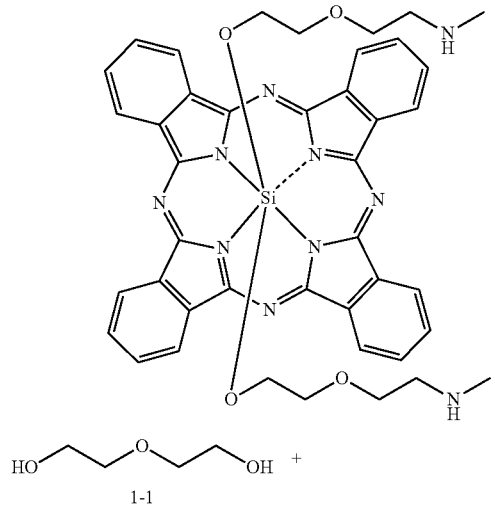

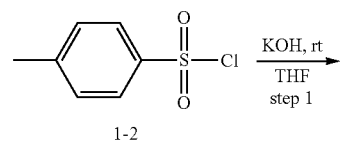

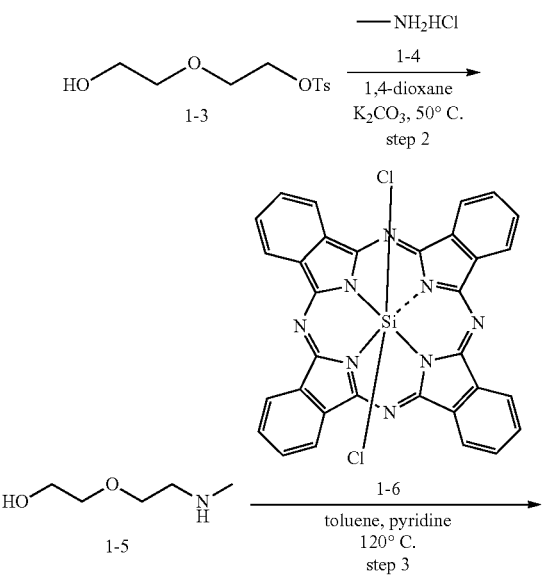

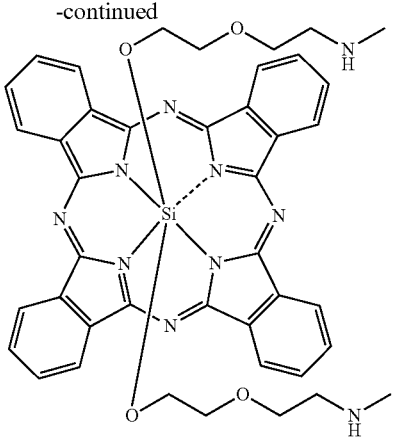

Step 1

Compound 1-1 (166 g, 1.57 mol) was dissolved in 500 mL of tetrahydrofuran, potassium hydroxide (32 g, 571 mmol) was added in an ice bath, and then p-toluenesulfonyl chloride 1-2 (100 g, 0.52 mol) was added in batches, and the mixture was stirred at room temperature for 5 hours. The reaction solution was poured into 1200 mL of water, (400 mL) and extracted twice with ethyl acetate. The extract liquid was combined and washed with saturated brine, dried over anhydrous sodium sulfate, and concentrated under reduced pressure and purified by silica gel column chromatography, with an eluent (petroleum ether:ethyl acetate=1:1), to obtain the target product 1-3 (55 g, 65%) as a colorless oil, LC-MS: m/z=261 [M+H]$^+$.

Step 2

Compound 1-3 (5.1 g, 19.6 mmol) was dissolved in 1,4-dioxane (50 mL), followed by addition of methylamine hydrochloride 1-4 (13.4 g, 196 mmol), and potassium carbonate (13.8 g, 100 mmol) was added under stirring in batches, followed by stirring the reaction overnight under conditions of 50° C. and a closed reaction system, TLC monitoring showed that the starting material 1-3 was completely reacted. The solvent was removed under reduced pressure to obtain a concentrated residue. The concentrated residue was dispensed with dichloromethane (20 mL), an appropriate amount of silica gel was added and the sample was stirred, spin-dried under reduced pressure and directly placed on a silica gel column for column chromatographic purification, with an eluent (dichloromethane:methanol=20/1-5/1) to obtain the target product 1-5 (1.2 g, 52%) as a pale yellow oil, LC-MS: m/z=120[M+H]$^+$.

Step 3

Compound 1-5 (260 mg, 2.18 mmol), compound 1-6 (445 mg, 0.73 mmol) (purchased from Aldrich Company, Product No. 287768) and 1.2 mL of pyridine were added into a 100 mL reaction flask, then toluene (25 mL) was added to the reaction system. The atmosphere of the reaction system was changed to a nitrogen atmosphere using nitrogen ball, the temperature was heated to 120° C., and the reaction was performed at 120° C. for 4 hours. The reaction system was cooled to room temperature, concentrated under reduced pressure, then 10 mL of water was added to the reaction system, and the resulting mixture was extracted three times with ethyl acetate (10 mL). The extract liquid was combined, washed with saturated brine, dried over anhydrous sodium sulfate, concentrated, and purified by silica gel column chromatography, with an eluent of ammoniated dichloromethane:methanol=100/3-50/1, to obtain the target product 1 (60 mg, 10.6%) as a deep blue solid. $^1$H NMR (400 MHz, CDCl$_3$): δ 9.66-9.63 (m, 8H), 8.37-8.34 (m, 8H), 1.96-1.92 (m, 4H), 1.75-1.71 (m, 10H), 0.43-0.40 (m, 4H), −1.89--1.90 (m, 4H). HRMS: 799.9205 [M+Na]$^+$.

EXAMPLE 2

27 mmol) was added under stirring potassium in batches, followed by stirring the reaction overnight under at 70° C., TLC monitoring showed that the starting material 1-3 was completely reacted. The solvent was removed under reduced pressure to obtain a concentrated residue. The concentrated residue was dispensed with dichloromethane (20 mL), an appropriate amount of silica gel was added and the sample was stirred, spin-dried under reduced pressure and directly placed on a silica gel column for column chromatographic purification, with an eluent (dichloromethane:methanol=20/1-5/1) to obtain the target product 2-2 (1.5 g, 83%) as a pale yellow oil, LC-MS: m/z=134[M+H]$^+$.

Step 2

Compound 2-2 (201 mg, 1.47 mmol), compound 1-6 (300 mg, 0.49 mmol) and sodium hydride (118 mg, 2.94 mmol, 60% w/w) were added into a 100 mL reaction flask, then toluene (20 mL) was added to the reaction system. The atmosphere of the reaction system was changed to a nitrogen atmosphere using nitrogen ball and the reaction was performed at room temperature for 5 hours. The reaction system was concentrated under reduced pressure, then 10 mL of water was added to the reaction system, and the resulting mixture was extracted three times with ethyl acetate (10 mL). The extract liquid was combined, washed with saturated brine, dried over anhydrous sodium sulfate, concentrated, and purified by silica gel column chromatography, with an eluent of ammoniated dichloromethane:methanol=100/3-50/1, to obtain the target product 2 (56 mg, 14.2%) as a deep blue solid. $^1$H NMR (400 MHz, CDCl$_3$): δ 9.68-9.64 (m, 8H), 8.38-8.34 (m, 8H), 2.17-2.11 (m, 4H), 1.75-1.68 (m, 8H), 0.83-0.80 (m, 6H), 0.41-0.38 (m, 4H), −1.86--1.89 (m, 4H). HRMS: 827.3210 [M+Na]$^+$.

EXAMPLE 3

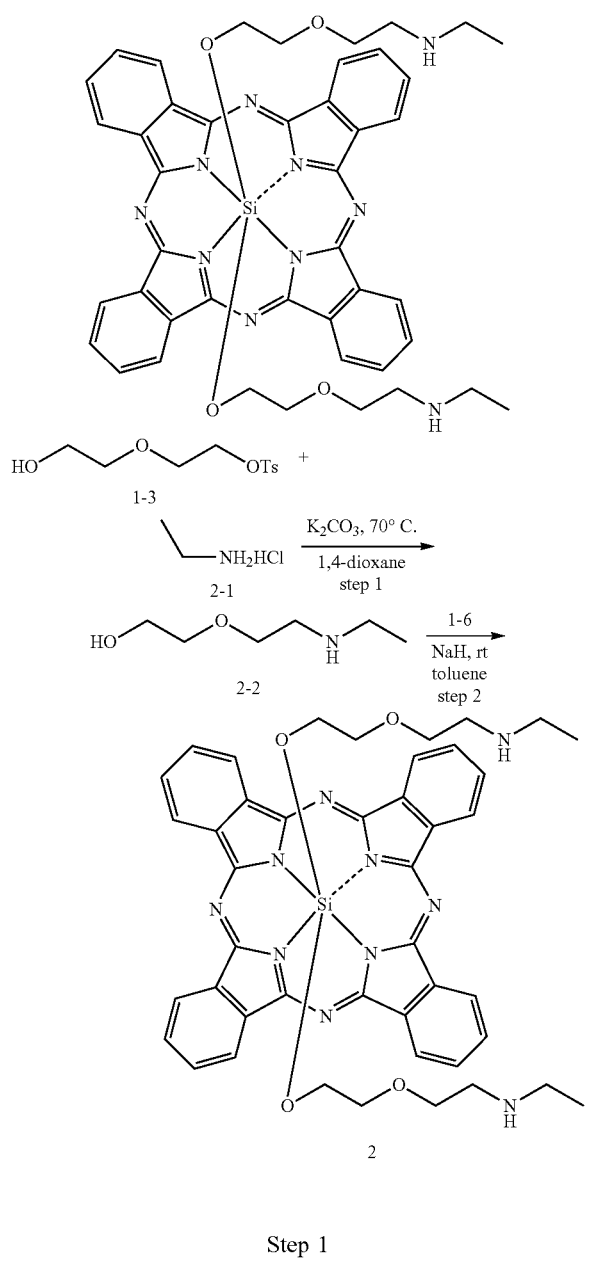

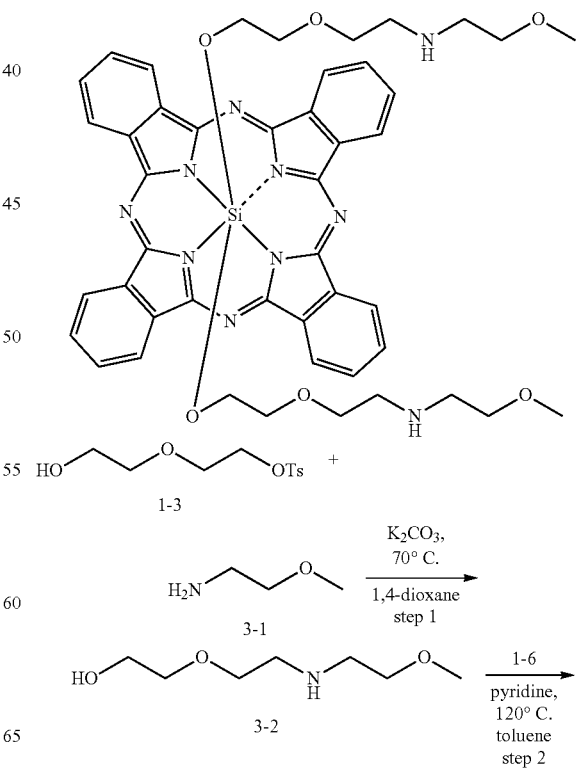

Step 1

Compound 1-3 (3.5 g, 13.5 mmol) was dissolved in 1,4-dioxane (50 mL), followed by addition of ethylamine hydrochloride 2-1 (2.2 g, 27 mmol), and carbonate (3.73 g,

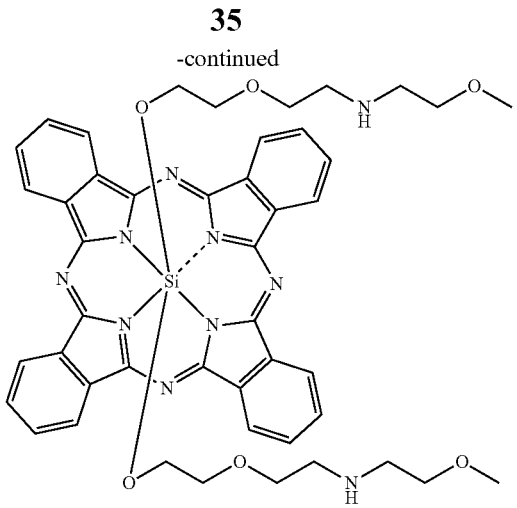

3

Step 1

Compound 1-3 (5.7 g, 22 mmol) was dissolved in 1,4-dioxane (60 mL), followed by addition of methoxyethylamine 3-1 (2 g, 27 mmol), and potassium carbonate (3.73 g, 27 mmol) was added under stirring in batches, followed by stirring the reaction overnight at 70° C., TLC monitoring showed that the starting material 1-3 was completely reacted. The solvent was removed under reduced pressure to obtain a concentrated residue. The concentrated residue was dispensed with dichloromethane (20 mL), an appropriate amount of silica gel was added and the sample was stirred, spin-dried under reduced pressure and directly placed on a silica gel column for column chromatographic purification, with an eluent (dichloromethane:methanol=20/1-5/1) to obtain the target product 3-2 (2.1 g, 58%) as a pale yellow oil, LC-MS: m/z=164[M+H]$^+$.

Step 2

Compound 3-2 (240 mg, 1.5 mmol), compound 1-6 (445 mg, 0.49 mmol) and 1.5 mL of pyridine were added into a 100 mL reaction flask, then toluene (30 mL) was added to the reaction system. The atmosphere of the reaction system was changed to a nitrogen atmosphere using nitrogen ball, the temperature was heated to 120° C., and the reaction was performed at 120° C. for 4 hours. The reaction system was cooled to room temperature, concentrated under reduced pressure, then 10 mL of water was added to the reaction system, and the resulting mixture was extracted three times with ethyl acetate (10 mL). The extract liquid was combined, washed with saturated brine, dried over anhydrous sodium sulfate, concentrated, and purified by silica gel column chromatography, with an eluent of ammoniated dichloromethane:methanol=100/3-50/1, to obtain the target product 3 (60 mg, 14.2%) as a deep blue solid. $^1$H NMR (400 MHz, CDCl$_3$): δ 9.67-9.65 (m, 8H), 8.37-8.35 (m, 8H), 3.19-3.15 (m, 10H), 2.27-2.25 (m, 4H), 1.72-1.67 (m, 8H), 0.40-0.37 (m, 4H), −1.87-−1.89 (m, 4H). HRMS: 887.3420 [M+Na]$^+$.

EXAMPLE 4

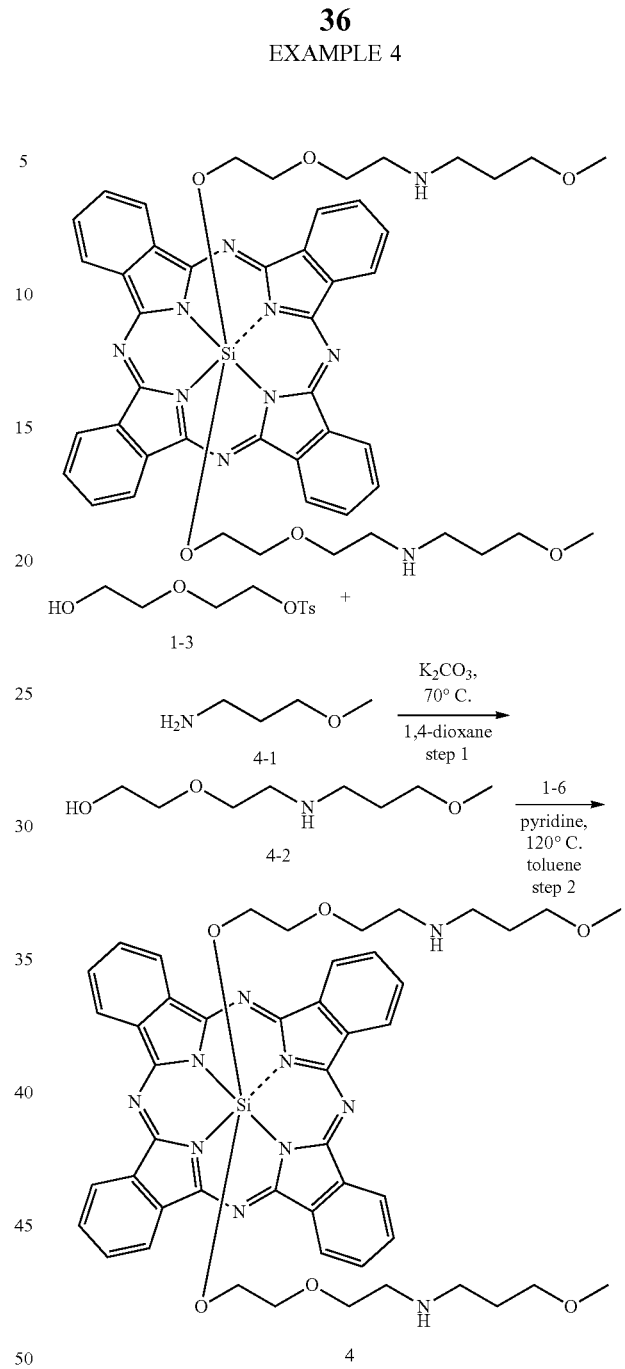

Step 1

Compound 1-3 (3.5 g, 13.5 mmol) was dissolved in 1,4-dioxane (50 mL), followed by addition of methoxypropylamine 4-1 (4.81 g, 54 mmol), and potassium carbonate (5.52 g, 40 mmol) was added under stirring in batches, followed by stirring the reaction overnight under at 70° C., TLC monitoring showed that the starting material 1-3 was completely reacted. The solvent was removed under reduced pressure to obtain a concentrated residue. The concentrated residue was dispensed with dichloromethane (20 mL), an appropriate amount of silica gel was added and the sample was stirred, spin-dried under reduced pressure and directly placed on a silica gel column for column chromatographic purification, with an eluent (dichloromethane:methanol=20/1-5/1) to obtain the target product 4-2 (1.6 g, 67%) as a pale yellow oil, LC-MS: m/z=178[M+H]$^+$.

Step 2

Compound 4-2 (265 mg, 1.5 mmol), compound 1-6 (300 mg, 0.49 mmol) and 1.5 mL of pyridine were added into a 100 mL reaction flask, then toluene (30 mL) was added to the reaction system. The atmosphere of the reaction system was changed to a nitrogen atmosphere using nitrogen ball, the temperature was heated to 120° C., and the reaction was performed at 120° C. for 4 hours. The reaction system was cooled to room temperature, concentrated under reduced pressure, then 10 mL of water was added to the reaction system, and the resulting mixture was extracted three times with ethyl acetate (10 mL). The extract liquid was combined, washed with saturated brine, dried over anhydrous sodium sulfate, concentrated, and purified by silica gel column chromatography, with an eluent of ammoniated dichloromethane:methanol=100/3-50/1, to obtain the target product 4 (129 mg, 29.5%) as a deep blue solid. $^1$H NMR (400 MHz, CDCl$_3$): δ 9.67-9.65 (m, 8H), 8.38-8.35 (m, 8H), 3.23-3.20 (m, 10H), 2.19-2.15 (m, 4H), 1.71-1.69 (m, 8H), 1.46-1.43 (m, 4H), 0.41-0.38 (m, 4H), −1.87-−1.90 (m, 4H). HRMS: 893.3913 [M+H]$^+$.

EXAMPLE 5

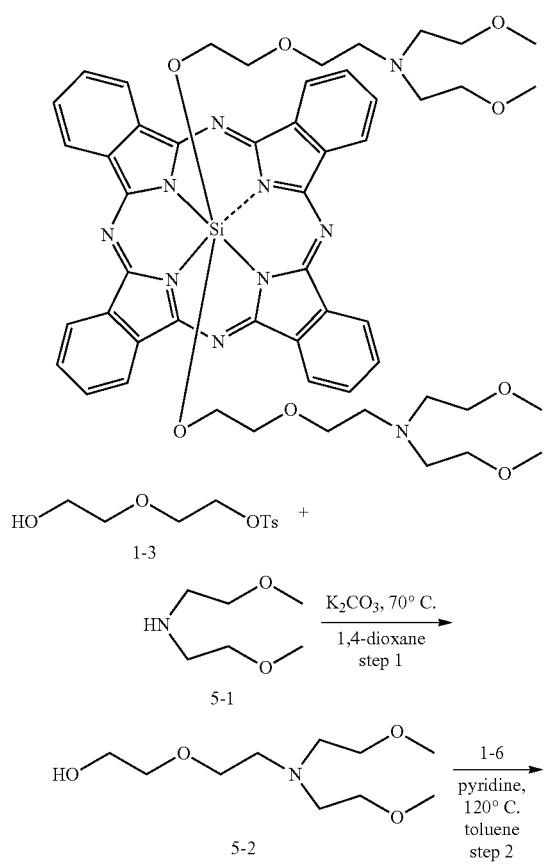

-continued

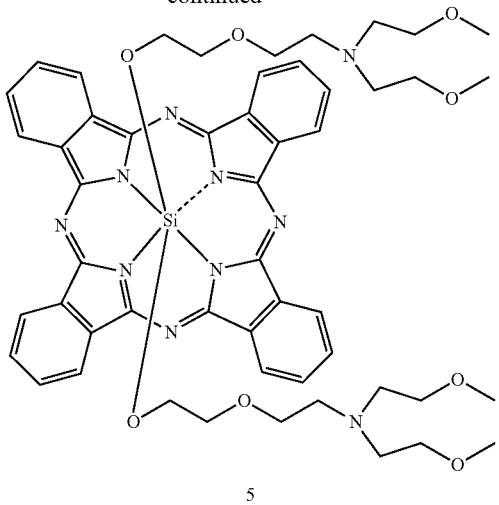

5

Step 1

Compound 1-3 (3.5 g, 13.5 mmol) was dissolved in 1,4-dioxane (50 mL), followed by addition of compound 5-1 (1.9 g, 14.2 mmol), and potassium carbonate (3.7 g, 27 mmol) was added under stirring in batches, followed by stirring the reaction overnight at 70° C., TLC monitoring showed that the starting material 1-3 was completely reacted. The solvent was removed under reduced pressure to obtain a concentrated residue. The concentrated residue was dispensed with dichloromethane (20 mL), an appropriate amount of silica gel was added and the sample was stirred, spin-dried under reduced pressure and directly placed on a silica gel column for column chromatographic purification, with an eluent (dichloromethane:methanol=20/1-5/1) to obtain the target product as a pale yellow oil 5-2 (1.2 g, 40%), LC-MS: m/z=222[M+H]$^+$.

Step 2

Compound 5-2 (198 mg, 0.89 mmol), compound 1-6 (182 mg, 0.3 mmol) and 1 mL of pyridine were added into a 100 mL reaction flask, then toluene (30 mL) was added to the reaction system. The atmosphere of the reaction system was changed to a nitrogen atmosphere using nitrogen ball, the temperature was heated to 120° C., and the reaction was performed at 120° C. for 4 hours. The reaction system was cooled to room temperature, concentrated under reduced pressure, then 10 mL of water was added to the reaction system, and the resulting mixture was extracted three times with ethyl acetate (10 mL). The extract liquid was combined, washed with saturated brine, dried over anhydrous sodium sulfate, concentrated, and purified by silica gel column chromatography, with an eluent of ammoniated dichloromethane:methanol=100/3-50/1, to obtain the target product 5 (69 mg, 23.5%) as a deep blue solid. $^1$H NMR (400 MHz, CDCl$_3$): δ 9.67-9.65 (m, 8H), 8.38-8.36 (m, 8H), 3.11-3.02 (m, 16H), 2.16-2.12 (m, 8H), 1.75-1.61 (m, 12H), 0.39-0.35 (m, 4H), −1.90-−1.92 (m, 4H); HRMS: 1003.4255 [M+Na]$^+$.

EXAMPLE 6

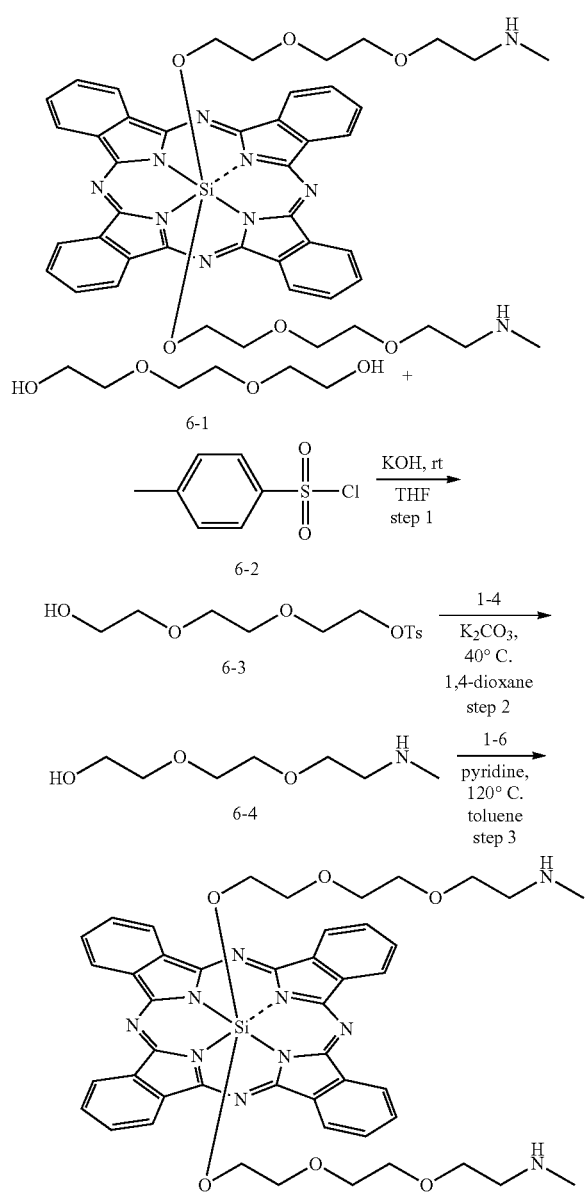

Step 1

Compound 6-1 (235 g, 1.57 mol) was dissolved in 500 mL of tetrahydrofuran, then potassium hydroxide (41.2 g, 0.57 mmol, 82% w/w) was added, and then p-toluenesulfonyl chloride 6-2 (100 g, 0.52 mol) was added in batches, and the mixture was stirred at room temperature for 5 hours. The reaction solution was poured into 1200 mL of water, and extracted with ethyl acetate (400 mL*3). The extract liquid was combined and washed with saturated brine, dried over anhydrous sodium sulfate, and concentrated under reduced pressure and purified by silica gel column chromatography, with an eluent (petroleum ether:ethyl acetate=1:1), to obtain the target product 6-3 (118 g, 75%) as a colorless oil. LC-MS: m/z=305[M+H]$^+$.

Step 2

Compound 6-3 (5.3 g, 17.4 mmol) was dissolved in 1,4-dioxane (60 mL), followed by addition of compound 1-4 (3.5 g, 52 mmol), and potassium carbonate (4.9 g, 35.8 mmol) was added under stirring in batches, followed by stirring the reaction overnight at 40° C., TLC monitoring showed that the starting material 6-3 was completely reacted. The solvent was removed under reduced pressure to obtain a concentrated residue. The concentrated residue was dispensed with dichloromethane (20 mL), an appropriate amount of silica gel was added and the sample was stirred, spin-dried under reduced pressure and directly placed on a silica gel column for column chromatographic purification, with an eluent (dichloromethane:methanol=20/1-5/1) to obtain the target product 6-4 (1.2 g, 42%) as a pale yellow oil, LC-MS: m/z=164[M+H]$^+$.

Step 3

Compound 6-4 (240 mg, 1.5 mmol), compound 1-6 (300 mg, 0.49 mmol) and 1.5 mL of pyridine were added into a 100 mL reaction flask, then toluene (30 mL) was added to the reaction system. The atmosphere of the reaction system was changed to a nitrogen atmosphere using nitrogen ball, the temperature was heated to 120° C., and the reaction was performed at 120° C. for 4 hours. The reaction system was cooled to room temperature, concentrated under reduced pressure, then 10 mL of water was added to the reaction system, and the resulting mixture was extracted three times with ethyl acetate (10 mL). The extract liquid was combined, washed with saturated brine, dried over anhydrous sodium sulfate, concentrated, and purified by silica gel column chromatography, with an eluent of ammoniated dichloromethane:methanol=100/3-50/1, to obtain the target product 6 (27 mg, 6.4%) as a deep blue solid. $^1$H NMR (400 MHz, CDCl$_3$): δ 9.65-9.63 (m, 8H), 8.37-8.34 (m, 8H), 3.60-3.56 (m, 10H), 2.99-2.95 (m, 2H), 2.45-2.41 (m, 6H), 2.12-2.10 (m, 4H), 0.43-0.39 (m, 4H), −1.87--1.91 (m, 4H); HRMS: 865.0365 [M]$^+$.

EXAMPLE 7

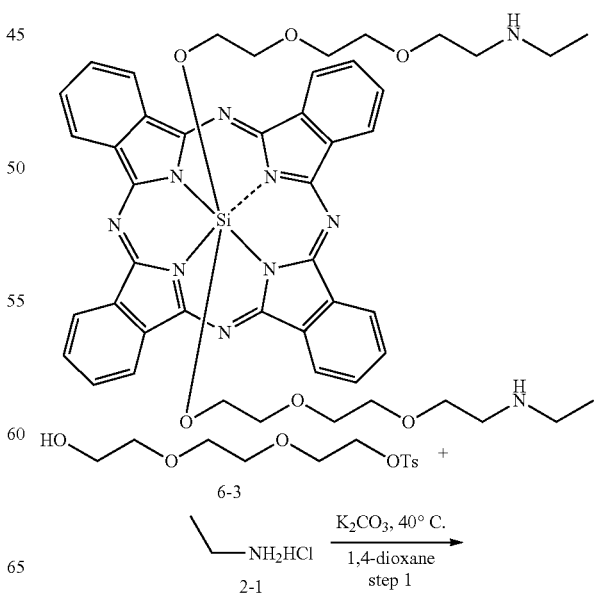

EXAMPLE 8

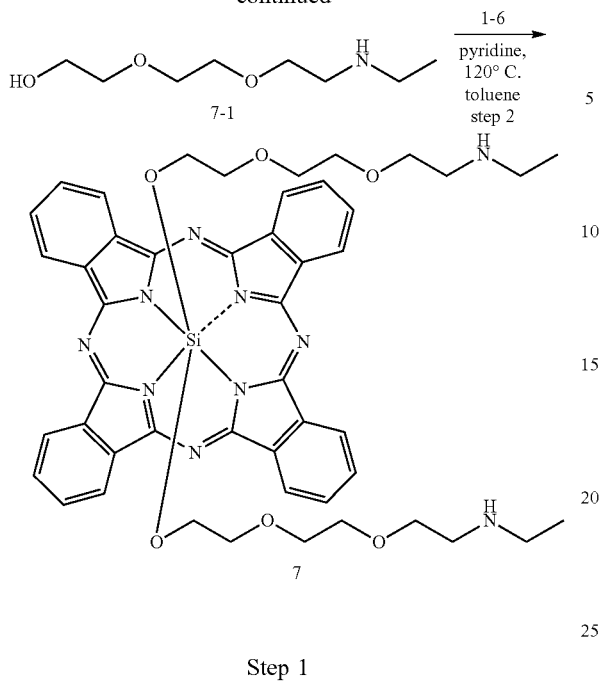

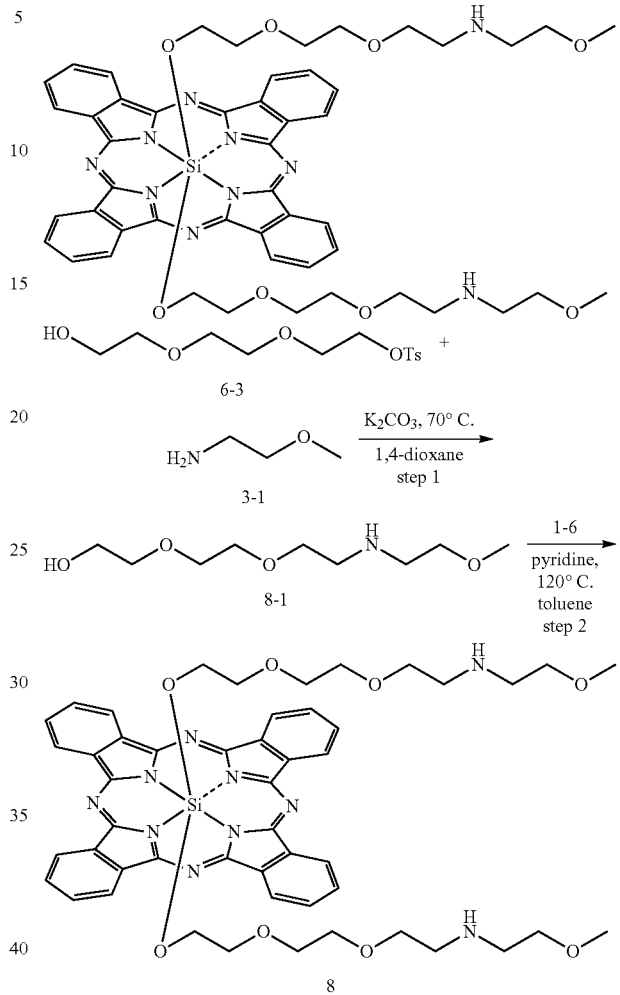

Step 1

Compound 6-3 (5.3 g, 17.4 mmol) was dissolved in 1,4-dioxane (60 mL), followed by addition of compound 2-1 (4.24 g, 52 mmol), and potassium carbonate (4.9 g, 35.8 mmol) was added under stirring in batches, followed by stirring the reaction overnight at 40° C., TLC monitoring showed that the starting material 6-3 was completely reacted. The solvent was removed under reduced pressure to obtain a concentrated residue. The concentrated residue was dispensed with dichloromethane (20 mL), an appropriate amount of silica gel was added and the sample was stirred, spin-dried under reduced pressure and directly placed on a silica gel column for column chromatographic purification, with an eluent (dichloromethane:methanol=20/1-5/1) to obtain the target product 7-1 (1.4 g, 45%) as a pale yellow oil, LC-MS: m/z=178[M+H]$^+$.

Step 2

Compound 7-1 (250 mg, 1.5 mmol), compound 1-6 (300 mg, 0.49 mmol) and 1.5 mL of pyridine were added into a 100 mL reaction flask, then toluene (30 mL) was added to the reaction system. The atmosphere of the reaction system was changed to a nitrogen atmosphere using nitrogen ball, the temperature was heated to 120° C., and the reaction was performed at 120° C. for 4 hours. The reaction system was cooled to room temperature, concentrated under reduced pressure, then 10 mL of water was added to the reaction system, and the resulting mixture was extracted three times with ethyl acetate (10 mL). The extract liquid was combined, washed with saturated brine, dried over anhydrous sodium sulfate, concentrated, and purified by silica gel column chromatography, with an eluent of ammoniated dichloromethane:methanol=100/3-50/1, to obtain the target product 7 (65 mg, 14.8%) as a deep blue solid. $^1$H NMR (400 MHz, CDCl$_3$): δ 9.67-9.64 (m, 8H), 8.38-8.36 (m, 8H), 2.99-2.97 (m, 4H), 2.41-2.34 (m, 12H), 1.66-1.64 (m, 4H), 0.89-0.86 (m, 6H), 0.45-0.43 (m, 4H), −1.87--1.90 (m, 4H); HRMS: 893.3912 [M+H]$^+$.

Step 1

Compound 6-3 (5.3 g, 17.4 mmol) was dissolved in 1,4-dioxane (60 mL), followed by addition of compound 3-1 (3.9 g, 52 mmol), and potassium carbonate (4.9 g, 34.8 mmol) was added under stirring in batches, followed by stirring the reaction overnight at 70° C., TLC monitoring showed that the starting material 6-3 was completely reacted. The solvent was removed under reduced pressure to obtain a concentrated residue. The concentrated residue was dispensed with dichloromethane (20 mL), an appropriate amount of silica gel was added and the sample was stirred, spin-dried under reduced pressure and directly placed on a silica gel column for column chromatographic purification, with an eluent (dichloromethane:methanol=20/1-5/1) to obtain the target product 8-1 (1.6 g, 44%) as a pale yellow oil, LC-MS: m/z=208[M+H]$^+$.

Step 2

Compound 8-1 (310 mg, 1.5 mmol), compound 1-6 (300 mg, 0.49 mmol) and 1.5 mL of pyridine were added into a 100 mL reaction flask, then toluene (30 mL) was added to the reaction system. The atmosphere of the reaction system was changed to a nitrogen atmosphere using nitrogen ball, the temperature was heated to 120° C., and the reaction was performed at 120° C. for 4 hours. The reaction system was cooled to room temperature, concentrated under reduced pressure, then 10 mL of water was added to the reaction system, and the resulting mixture was extracted three times with ethyl acetate (10 mL). The extract liquid was combined, washed with saturated brine, dried over anhydrous sodium sulfate, concentrated, and purified by silica gel column chromatography, with an eluent of ammoniated dichloromethane:methanol=100/3-50/1, to obtain the target product 8 (82 mg, 17.6%) as a deep blue solid. $^1$H NMR (400 MHz, CDCl$_3$): δ 9.65-9.62 (m, 8H), 8.37-8.34 (m, 8H), 3.34-3.30 (m, 4H), 3.23 (s, 6H), 2.97-2.94 (m, 4H), 2.58-2.56 (m, 4H), 2.43-2.41 (m, 8H), 1.67-1.64 (m, 4H), 0.45-0.41 (m, 4H), −1.86--1.89 (m, 4H); HRMS: 975.3945 [M+Na]$^+$.

EXAMPLE 9

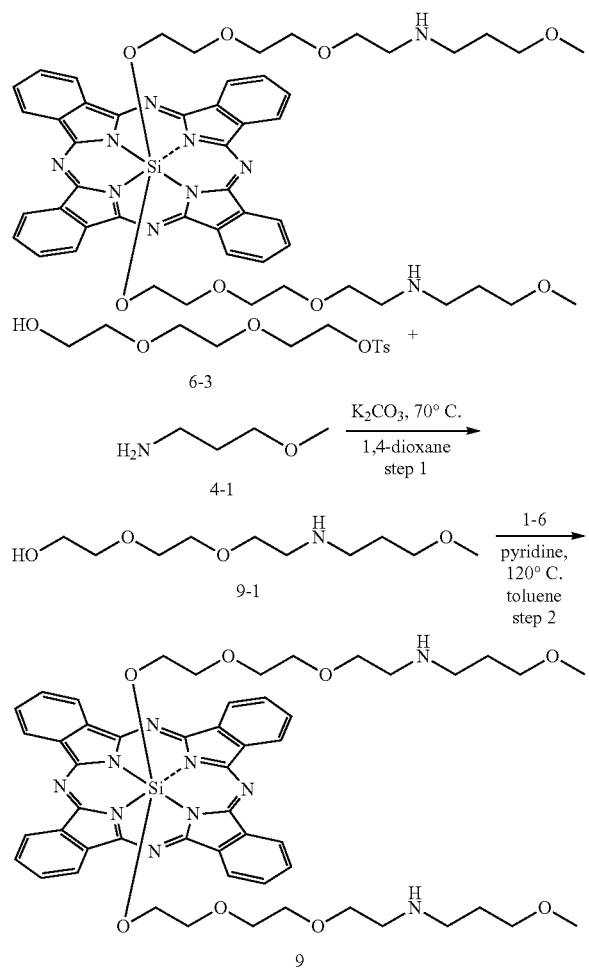

Step 1

Compound 6-3 (5.3 g, 17.4 mmol) was dissolved in 1,4-dioxane (60 mL), followed by addition of compound 4-1 (3.9 g, 52 mmol), and potassium carbonate (4.9 g, 34.8 mmol) was added under stirring in batches, followed by stirring the reaction overnight at 70° C., TLC monitoring showed that the starting material 6-3 was completely reacted. The solvent was removed under reduced pressure to obtain a concentrated residue. The concentrated residue was dispensed with dichloromethane (20 mL), an appropriate amount of silica gel was added and the sample was stirred, spin-dried under reduced pressure and directly placed on a silica gel column for column chromatographic purification, with an eluent (dichloromethane:methanol=20/1-5/1) to obtain the target product 9-1 (1.8 g, 46%) as a pale yellow oil, LC-MS: m/z=222[M+H]$^+$.

Step 2

Compound 9-1 (324 mg, 1.5 mmol), compound 1-6 (300 mg, 0.49 mmol) and 1.5 mL of pyridine were added into a 100 mL reaction flask, then toluene (30 mL) was added to the reaction system. The atmosphere of the reaction system was changed to a nitrogen atmosphere using nitrogen ball, the temperature was heated to 120° C., and the reaction was performed at 120° C. for 4 hours. The reaction system was cooled to room temperature, concentrated under reduced pressure, then 10 mL of water was added to the reaction system, and the resulting mixture was extracted three times with ethyl acetate (10 mL). The extract liquid was combined, washed with saturated brine, dried over anhydrous sodium sulfate, concentrated, and purified by silica gel column chromatography, with an eluent of ammoniated dichloromethane:methanol=100/3-50/1, to obtain the target product 9 (72 mg, 15%) as a deep blue solid. $^1$H NMR (400 MHz, CDCl$_3$): δ 9.66-9.64 (m, 8H), 8.38-8.35 (m, 8H), 3.30-3.27 (m, 4H), 3.21 (s, 6H), 2.97-2.94 (m, 4H), 2.45-2.39 (m, 12H), 1.66-1.63 (m, 4H), 1.60-1.56 (m, 4H), 0.45-0.41 (m, 4H), −1.86--1.89 (m, 4H); HRMS: 975.3945 [M+Na]$^+$.

EXAMPLE 10

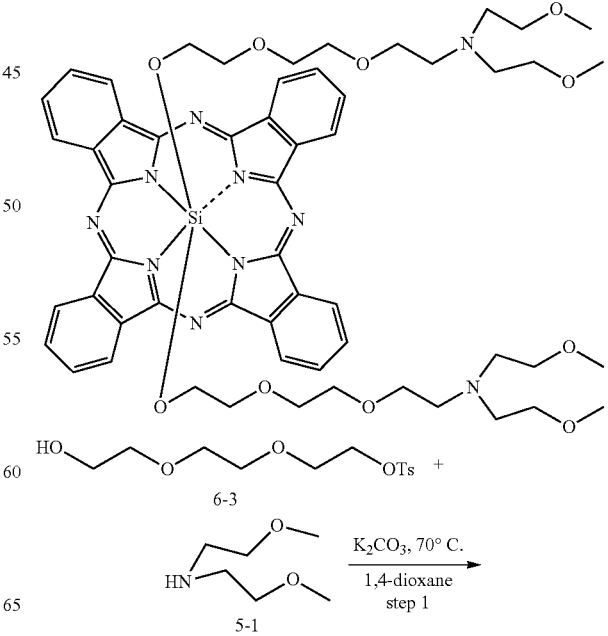

45
-continued

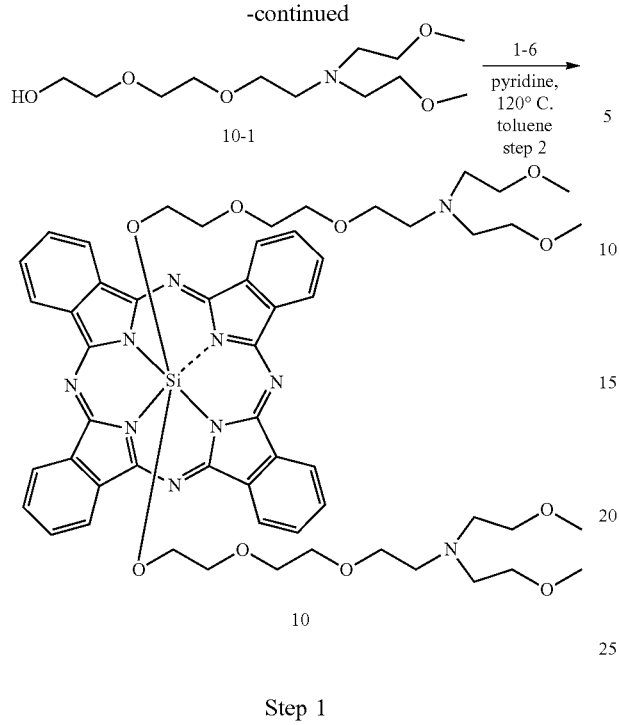

Step 1

Compound 6-3 (5.3 g, 17.4 mmol) was dissolved in 1,4-dioxane (60 mL), followed by addition of compound 5-1 (4.85 g, 36.5 mmol), and potassium carbonate (4.9 g, 34.8 mmol) was added under stirring in batches, followed by stirring the reaction overnight at 70° C., TLC monitoring showed that the starting material 6-3 was completely reacted. The solvent was removed under reduced pressure to obtain a concentrated residue. The concentrated residue was dispensed with dichloromethane (20 mL), an appropriate amount of silica gel was added and the sample was stirred, spin-dried under reduced pressure and directly placed on a silica gel column for column chromatographic purification, with an eluent (dichloromethane:methanol=20/1-5/1) to obtain the target product 10-1 (2.2 g, 47.7%) as a pale yellow oil, LC-MS: m/z=266[M+H]$^+$.

Step 2

Compound 10-1 (265 mg, 1 mmol), compound 1-6 (200 mg, 0.33 mmol) and 1 mL of pyridine were added into a 100 mL reaction flask, then toluene (30 mL) was added to the reaction system. The atmosphere of the reaction system was changed to a nitrogen atmosphere using nitrogen ball, the temperature was heated to 120° C., and the reaction was performed at 120° C. for 4 hours. The reaction system was cooled to room temperature, concentrated under reduced pressure, then 10 mL of water was added to the reaction system, and the resulting mixture was extracted three times with ethyl acetate (10 mL). The extract liquid was combined, washed with saturated brine, dried over anhydrous sodium sulfate, concentrated, and purified by silica gel column chromatography, with an eluent of ammoniated dichloromethane:methanol=100/3-50/1, to obtain the target product 10 (100 mg, 28.4%) as a deep blue solid. $^1$H NMR (400 MHz, CDCl$_3$): δ 9.67-9.64 (m, 8H), 8.38-8.36 (m, 8H), 3.30-3.27 (m, 8H), 3.22 (s, 12H), 2.97-2.94 (m, 4H), 2.55-2.52 (m, 6H), 2.44-2.42 (m, 10H), 1.67-1.65 (m, 4H), 0.42-0.39 (m, 4H), −1.87--1.90 (m, 4H); HRMS: 1091.4779 [M+Na]$^+$.

46
EXAMPLE 11

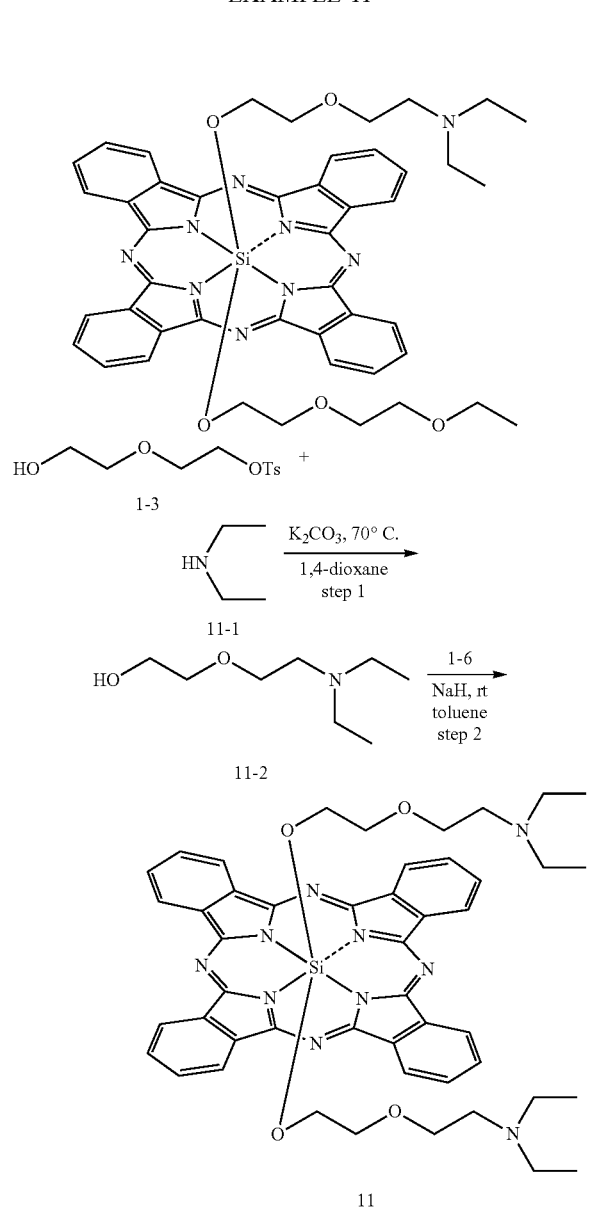

Step 1

Compound 1-3 (2.6 g, 10 mmol) was dissolved in 1,4-dioxane (40 mL), followed by addition of diethylamine 11-1 (2.2 g, 30 mmol), and potassium carbonate (2.76 g, 20 mmol) was added under stirring, followed by stirring the reaction overnight under conditions of 70° C. and a closed reaction system, TLC monitoring showed that the starting material 1-3 was completely reacted. The solvent was removed under reduced pressure to obtain a concentrated residue. The concentrated residue was dispensed with dichloromethane (20 mL), an appropriate amount of silica gel was added and the sample was stirred, spin-dried under reduced pressure and directly placed on a silica gel column for column chromatographic purification, with an eluent (dichloromethane:methanol=20/1-5/1) to obtain the target product 11-2 (0.68 g, 42%) as a pale yellow oil, LC-MS: m/z=162[M+H]$^+$.

Step 2

Compound 11-2 (140 mg, 0.87 mmol), compound 1-6 (265 mg, 0.43 mmol) and sodium hydride (70 mg, 1.75 mmol, 60% w/w) were added into a 100 mL reaction flask, then toluene (20 mL) was added to the reaction system. The atmosphere of the reaction system was changed to a nitrogen atmosphere using nitrogen ball and the reaction was performed at room temperature and monitored by TLC. After TLC showed that compound 1-6 was completely conversed, the reaction system was concentrated under reduced pressure, then 10 mL of water was added to the reaction system, and the resulting mixture was extracted three times with ethyl acetate (10 mL). The extract liquid was combined, washed with saturated brine, dried over anhydrous sodium sulfate, concentrated, and purified by silica gel column chromatography, with an eluent of ammoniated dichloromethane:methanol=100/3-50/1, to obtain the target product 11 (70 mg, 18.9%) as a deep blue solid. $^1$H NMR (500 MHz, CDCl$_3$): δ 9.63-9.61 (m, 8H), 8.34-8.32 (m, 8H), 1.91-1.88 (m, 8H), 1.63 (t, J=5 Hz, 4H), 1.47 (t, J=5 Hz, 4H), 0.57 (t, J=5 Hz, 12H), 0.35-0.33 (m, 4H), −1.91-−1.94 (m, 4H); HRMS: 883.3833 [M+Na]$^+$.

EXAMPLE 12

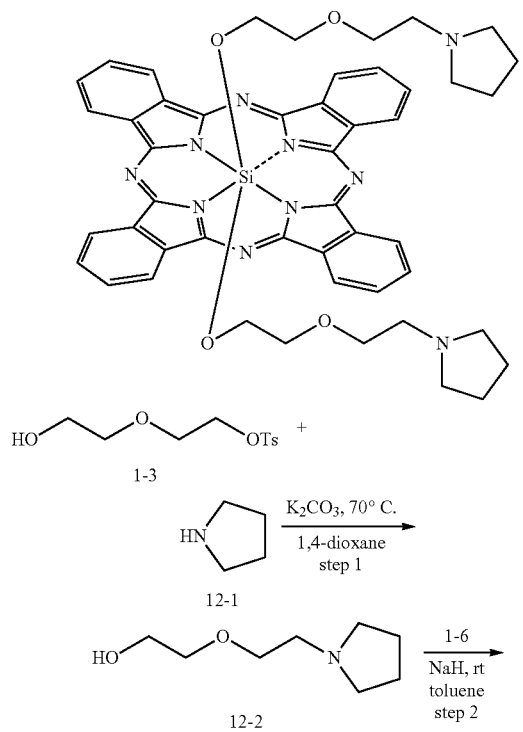

Step 1

Compound 1-3 (2.6 g, 10 mmol) was dissolved in 1,4-dioxane (40 mL), followed by addition of tetrahydropyrrole 12-1 (2.14 g, 30 mmol), and potassium carbonate (2.76 g, 20 mmol) was added under stirring, followed by stirring the reaction overnight under conditions of 70° C. and a closed reaction system, TLC monitoring showed that the starting material 1-3 was completely reacted. The solvent was removed under reduced pressure to obtain a concentrated residue. The concentrated residue was dispensed with dichloromethane (20 mL), an appropriate amount of silica gel was added and the sample was stirred, spin-dried under reduced pressure and directly placed on a silica gel column for column chromatographic purification, with an eluent (dichloromethane:methanol=20/1-5/1) to obtain the target product 12-2 (0.71 g, 45%) as a pale yellow oil, LC-MS: m/z=160[M+H]$^+$.

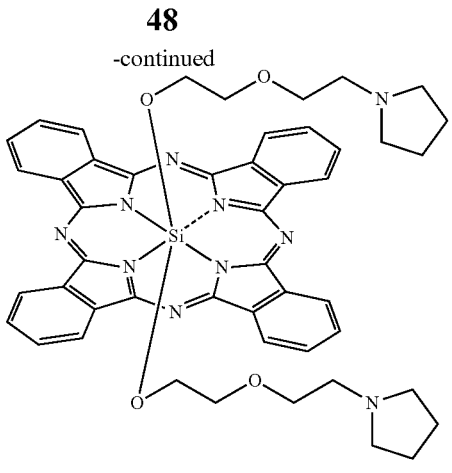

Step 2

Compound 12-2 (100 mg, 0.63 mmol), compound 1-6 (192 mg, 0.315 mmol) and sodium hydride (50 mg, 1.26 mmol, 60% w/w) were added into a 100 mL reaction flask, then toluene (20 mL) was added to the reaction system. The atmosphere of the reaction system was changed to a nitrogen atmosphere using nitrogen ball and the reaction was performed at room temperature and monitored by TLC. After TLC showed that compound 1-6 was completely conversed, the reaction system was concentrated under reduced pressure, then 10 mL of water was added to the reaction system, and the resulting mixture was extracted three times with ethyl acetate (10 mL). The extract liquid was combined, washed with saturated brine, dried over anhydrous sodium sulfate, concentrated, and purified by silica gel column chromatography, with an eluent of ammoniated dichloromethane:methanol=100/3-50/1, to obtain the target product 12 (30 mg, 11.2%) as a deep blue solid.

| Reaction batch | Compound 12-2 | Compound 1-6 | Target product 12 | Yield |
|---|---|---|---|---|
| 1 | 100 mg | 192 mg | 30 mg | 11.2% |
| 2 | 100 mg | 192 mg | 28 mg | 10.4% |

¹H NMR (500 MHz, CDCl₃): δ 9.64-9.61 (m, 8H), 8.34-8.32 (m, 8H), 1.82-1.76 (m, 8H), 1.65-1.62 (m, 4H), 1.48-1.44 (m, 12H), 0.36 (t, J=5 Hz, 4H), −1.92 (t, 4H, J=7.5 Hz). HRMS: 879.3520 [M+Na]⁺.

EXAMPLE 13

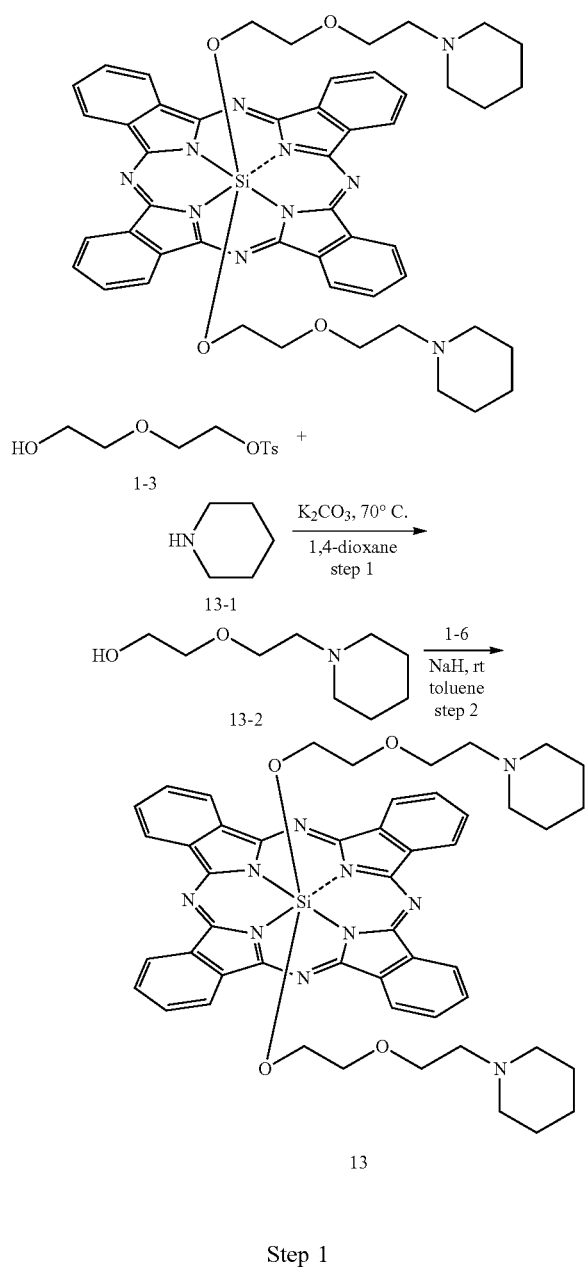

Step 1

Compound 1-3 (2.6 g, 10 mmol) was dissolved in 1,4-dioxane (40 mL), followed by addition of piperidine 13-1 (2.52 g, 30 mmol), and potassium carbonate (2.76 g, 20 mmol) was added under stirring, followed by stirring the reaction overnight under conditions of 70° C. and a closed reaction system, TLC monitoring showed that the starting material 1-3 was completely reacted. The solvent was removed under reduced pressure to obtain a concentrated residue. The concentrated residue was dispensed with dichloromethane (20 mL), an appropriate amount of silica gel was added and the sample was stirred, spin-dried under reduced pressure and directly placed on a silica gel column for column chromatographic purification, with an eluent (dichloromethane:methanol=20/1-5/1) to obtain the target product 13-2 (0.73 g, 42%) as a pale yellow oil, LC-MS: m/z=174[M+H]⁺.

Step 2

Compound 13-2 (150 mg, 0.867 mmol), compound 1-6 (265 mg, 0.433 mmol) and sodium hydride (70 mg, 1.74 mmol, 60% w/w) were added into a 100 mL reaction flask, then toluene (25 mL) was added to the reaction system. The atmosphere of the reaction system was changed to a nitrogen atmosphere using nitrogen ball and the reaction was performed at room temperature and monitored by TLC. After TLC showed that compound 1-6 was completely conversed, the reaction system was concentrated under reduced pressure, then 10 mL of water was added to the reaction system, and the resulting mixture was extracted three times with ethyl acetate (10 mL). The extract liquid was combined, washed with saturated brine, dried over anhydrous sodium sulfate, concentrated, and purified by silica gel column chromatography, with an eluent of ammoniated dichloromethane:methanol=100/3-50/1, to obtain the target product 13 (58 mg, 15.1%) as a deep blue solid. ¹H NMR (500 MHz, CDCl₃): δ 9.63-9.62 (m, 8H), 8.34-8.32 (m, 8H), 1.72-1.66 (m, 8H), 1.63 (t, J=7.5 Hz, 4H), 1.34 (t, J=5 Hz, 4H), 1.25-1.23 (m, 12H), 0.34 (t, J=5 Hz, 4H), −1.93 (t, J=7.5 Hz, 4H). HRMS: 907.3834 [M+Na]⁺.

EXAMPLE 14

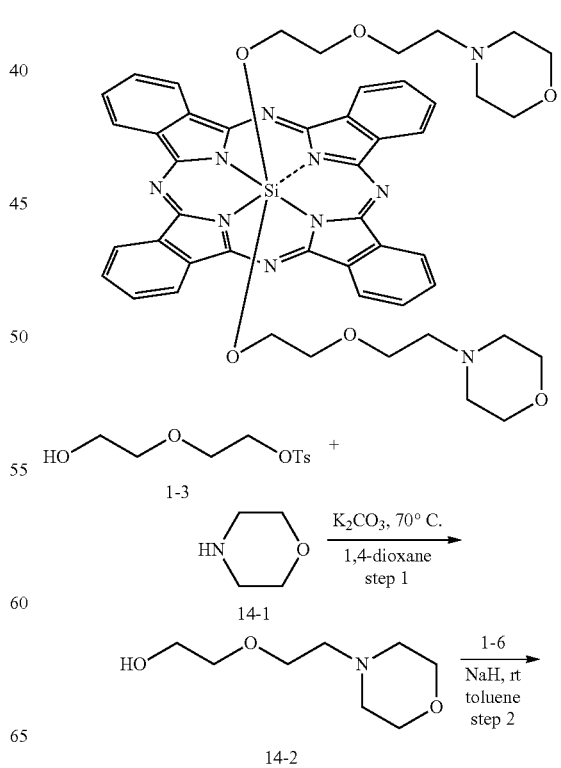

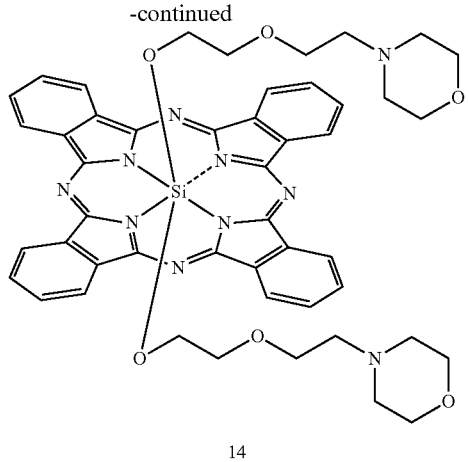

14

Step 1

Compound 1-3 (2.6 g, 10 mmol) was dissolved in 1,4-dioxane (50 mL), followed by addition of morpholine 14-1 (2.61 g, 30 mmol), and potassium carbonate (2.76 g, 20 mmol) was added under stirring, followed by stirring the reaction overnight under conditions of 70° C. and a closed reaction system, TLC monitoring showed that the starting material 1-3 was completely reacted. The solvent was removed under reduced pressure to obtain a concentrated residue. The concentrated residue was dispensed with dichloromethane (20 mL), an appropriate amount of silica gel was added and the sample was stirred, spin-dried under reduced pressure and directly placed on a silica gel column for column chromatographic purification, with an eluent (dichloromethane:methanol=20/1-5/1) to obtain the target product 14-2 (1 g, 57.1%) as a pale yellow oil, LC-MS: m/z=176[M+H]$^+$.

Step 2

Compound 14-2 (150 mg, 0.856 mmol), compound 1-6 (262 mg, 0.428 mmol) and sodium hydride (68 mg, 1.7 mmol, 60% w/w) were added into a 100 mL reaction flask, then toluene (25 mL) was added to the reaction system. The atmosphere of the reaction system was changed to a nitrogen atmosphere using nitrogen ball and the reaction was performed at room temperature and monitored by TLC. After TLC showed that compound 1-6 was completely converted, the reaction system was concentrated under reduced pressure, then 10 mL of water was added to the reaction system, and the resulting mixture was extracted three times with ethyl acetate (10 mL). The extract liquid was combined, washed with saturated brine, dried over anhydrous sodium sulfate, concentrated, and purified by silica gel column chromatography, with an eluent of ammoniated dichloromethane:methanol=100/3-50/1, to obtain the target product 14 (52 mg, 13.6%) as a deep blue solid. $^1$H NMR (500 MHz, CDCl$_3$): δ 9.64-9.62 (m, 8H), 8.35-8.34 (m, 8H), 3.38-3.32 (m, 8H), 1.73-1.68 (m, 8H), 1.35-1.33 (m, 8H), 0.38 (t, J=5 Hz, 4H), −1.93 (t, J=5 Hz, 4H). HRMS: 911.3417 [M+Na]$^+$.

EXAMPLE 15

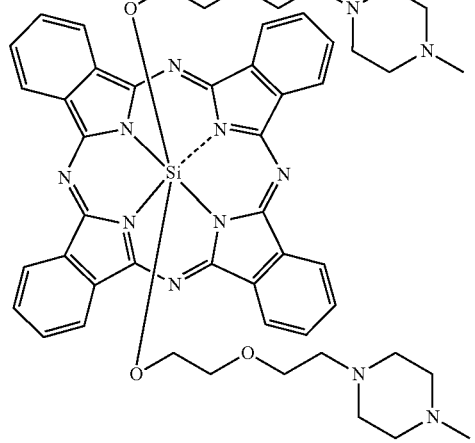

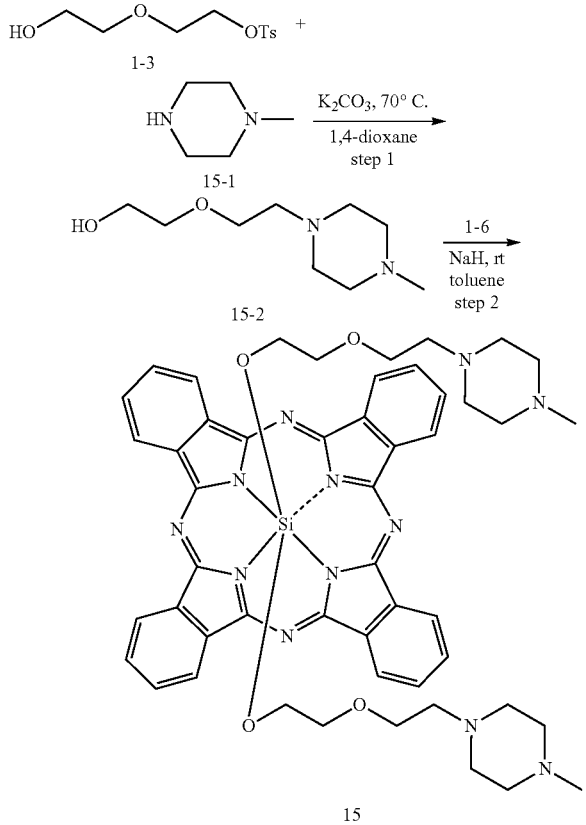

15

Step 1

Compound 1-3 (2.6 g, 10 mmol) was dissolved in 1,4-dioxane (50 mL), followed by addition of N-methylpiperazine 15-1 (3 g, 30 mmol), and potassium carbonate (2.76 g, 20 mmol) was added under stirring, followed by stirring the reaction overnight under conditions of 70° C. and a closed reaction system, TLC monitoring showed that the starting material 1-3 was completely reacted. The solvent was removed under reduced pressure to obtain a concentrated residue. The concentrated residue was dispensed with dichloromethane (20 mL), an appropriate amount of silica gel was added and the sample was stirred, spin-dried under reduced pressure and directly placed on a silica gel column for column chromatographic purification, with an eluent (dichloromethane:methanol=20/1-5/1) to obtain the target product 15-2 (1.45 g, 77.1%) as a pale yellow oil, LC-MS: m/z=189[M+H]⁺.

Step 2

Compound 15-2 (100 mg, 0.53 mmol), compound 1-6 (163 mg, 0.265 mmol) and sodium hydride (84 mg, 2.1 mmol, 60% w/w) were added into a 100 mL reaction flask, then toluene (15 mL) was added to the reaction system. The atmosphere of the reaction system was changed to a nitrogen atmosphere using nitrogen ball and the reaction was performed at room temperature and monitored by TLC. After TLC showed that compound 1-6 was completely conversed, the reaction system was concentrated under reduced pressure, then 10 mL of water was added to the reaction system, and the resulting mixture was extracted three times with ethyl acetate (10 mL). The extract liquid was combined, washed with saturated brine, dried over anhydrous sodium sulfate, concentrated, and purified by silica gel column chromatography, with an eluent of ammoniated dichloromethane:methanol=100/3-50/1, to obtain the target product 15 (102 mg, 42.1%) as a deep blue solid. $^1$H NMR (500 MHz, CDCl$_3$): δ 9.63-9.61 (m, 8H), 8.34-8.32 (m, 8H), 2.15 (s, 6H), 1.82-1.78 (m, 8H), 1.59-1.55 (m, 12H), 1.38 (t, J=5 Hz, 4H), 0.36 (t, J=5 Hz, 4H), −1.93 (t, J=5 Hz, 4H); HRMS: 937.4049 [M+Na]⁺.

EXAMPLE 16

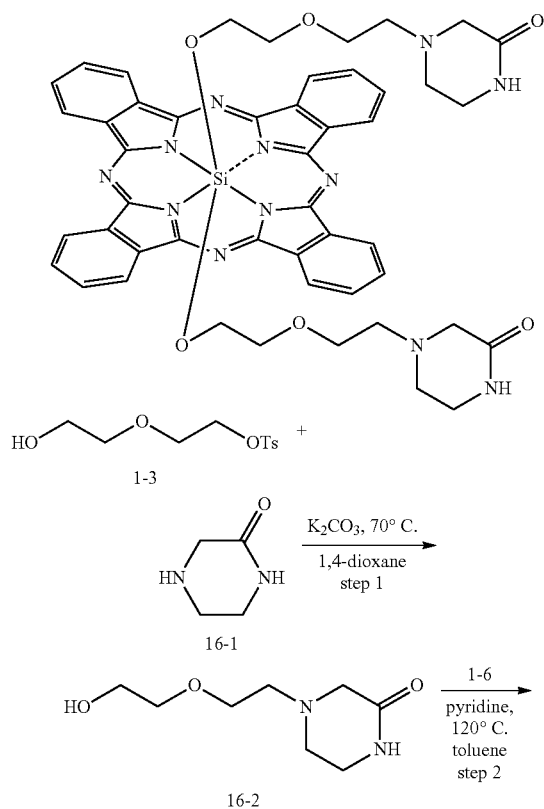

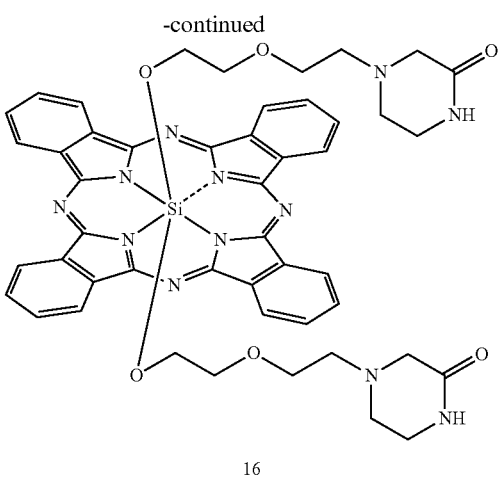

16

Step 1

Compound 1-3 (2.6 g, 10 mmol) was dissolved in 1,4-dioxane (50 mL), followed by addition of compound 16-1 (1 g, 10 mmol), and potassium carbonate (1.38 g, 10 mmol) was added under stirring, followed by stirring the reaction overnight under conditions of 70° C. and a closed reaction system, TLC monitoring showed that the starting material 1-3 was completely reacted. The solvent was removed under reduced pressure to obtain a concentrated residue. The concentrated residue was dispensed with dichloromethane (20 mL), an appropriate amount of silica gel was added and the sample was stirred, spin-dried under reduced pressure and directly placed on a silica gel column for column chromatographic purification, with an eluent (dichloromethane:methanol=20/1-5/1) to obtain the target product 16-2 (0.76 g, 40.4%) as a pale yellow oil, LC-MS: m/z=189[M+H]⁺.

Step 2

Compound 16-2 (100 mg, 0.532 mmol), compound 1-6 (163 mg, 0.266 mmol) and 0.5 mL of pyridine were added into a 100 mL reaction flask, then toluene (20 mL) was added to the reaction system. The atmosphere of the reaction system was changed to a nitrogen atmosphere using nitrogen ball, the temperature was heated to 120° C., and the reaction was performed at 120° C. for 4 hours. The reaction system was cooled to room temperature, concentrated under reduced pressure, then 10 mL of water was added to the reaction system, and the resulting mixture was extracted three times with ethyl acetate (10 mL). The extract liquid was combined, washed with saturated brine, dried over anhydrous sodium sulfate, concentrated, and purified by silica gel column chromatography, with an eluent of ammoniated dichloromethane:methanol=100/3-50/1, to obtain the target product 16 (55 mg, 22.6%) as a deep blue solid. $^1$H NMR (500 MHz, CDCl$_3$): δ 9.64-9.63 (m, 8H), 8.36-8.34 (m, 8H), 5.56-5.51 (m, 2H), 2.59-2.54 (m, 4H), 1.83 (t, J=5 Hz, 4H), 1.56-1.53 (m, 8H), 1.40 (t, J=5 Hz, 4H), 0.41 (t, J=5 Hz, 4H), −1.99 (t, J=5 Hz, 4H); HRMS: 937.3323 [M+Na]⁺.

EXAMPLE 17

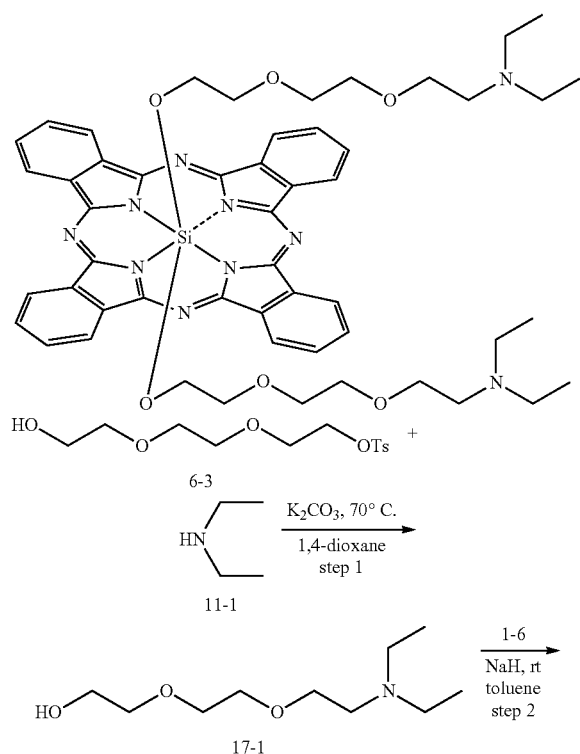

Step 1

Compound 6-3 (3.1 g, 10 mmol) was dissolved in 1,4-dioxane (50 mL), followed by addition of compound 11-1 (2.2 g, 30 mmol), and potassium carbonate (2.76 g, 20 mmol) was added under stirring, followed by stirring the reaction overnight at 40° C., TLC monitoring showed that the starting material 6-3 was completely reacted. The solvent was removed under reduced pressure to obtain a concentrated residue. The concentrated residue was dispensed with dichloromethane (20 mL), an appropriate amount of silica gel was added and the sample was stirred, spin-dried under reduced pressure and directly placed on a silica gel column for column chromatographic purification, with an eluent of (dichloromethane:methanol=20/1-5/1) to obtain the target product 17-1 (1 g, 48.8%) as a pale yellow oil, LC-MS: m/z=206[M+H]$^+$.

Step 2

Compound 17-1 (200 mg, 1 mmol), compound 1-6 (305 mg, 0.5 mmol) and sodium hydride (80 mg, 2 mmol, 60% w/w) were added into a 100 mL reaction flask, then toluene (25 mL) was added to the reaction system. The atmosphere of the reaction system was changed to a nitrogen atmosphere using nitrogen ball and the reaction was performed at room temperature and monitored by TLC. After TLC showed that compound 1-6 was completely conversed, the reaction system was concentrated under reduced pressure, then 10 mL of water was added to the reaction system, and the resulting mixture was extracted three times with ethyl acetate (10 mL). The extract liquid was combined, washed with saturated brine, dried over anhydrous sodium sulfate, concentrated, and purified by silica gel column chromatography, with an eluent of ammoniated dichloromethane:methanol=100/3-50/1, to obtain the target product 17 (88 mg, 18.6%) as a deep blue solid. $^1$H NMR (500 MHz, CDCl$_3$): δ 9.67-9.64 (m, 8H), 8.34-8.30 (m, 8H), 2.90 (t, J=7.5 Hz, 4H), 2.39 (t, J=7.5 Hz, 4H), 2.31-2.27 (m, 8H), 2.20 (t, J=5 Hz, 4H), 1.64-1.60 (m, 4H), 0.81 (t, J=7.5 Hz, 12H), 0.37 (t, J=5 Hz, 4H,), −1.92 (t, J=5 Hz, 4H); HRMS: 949.4538 [M+H]$^+$.

EXAMPLE 18

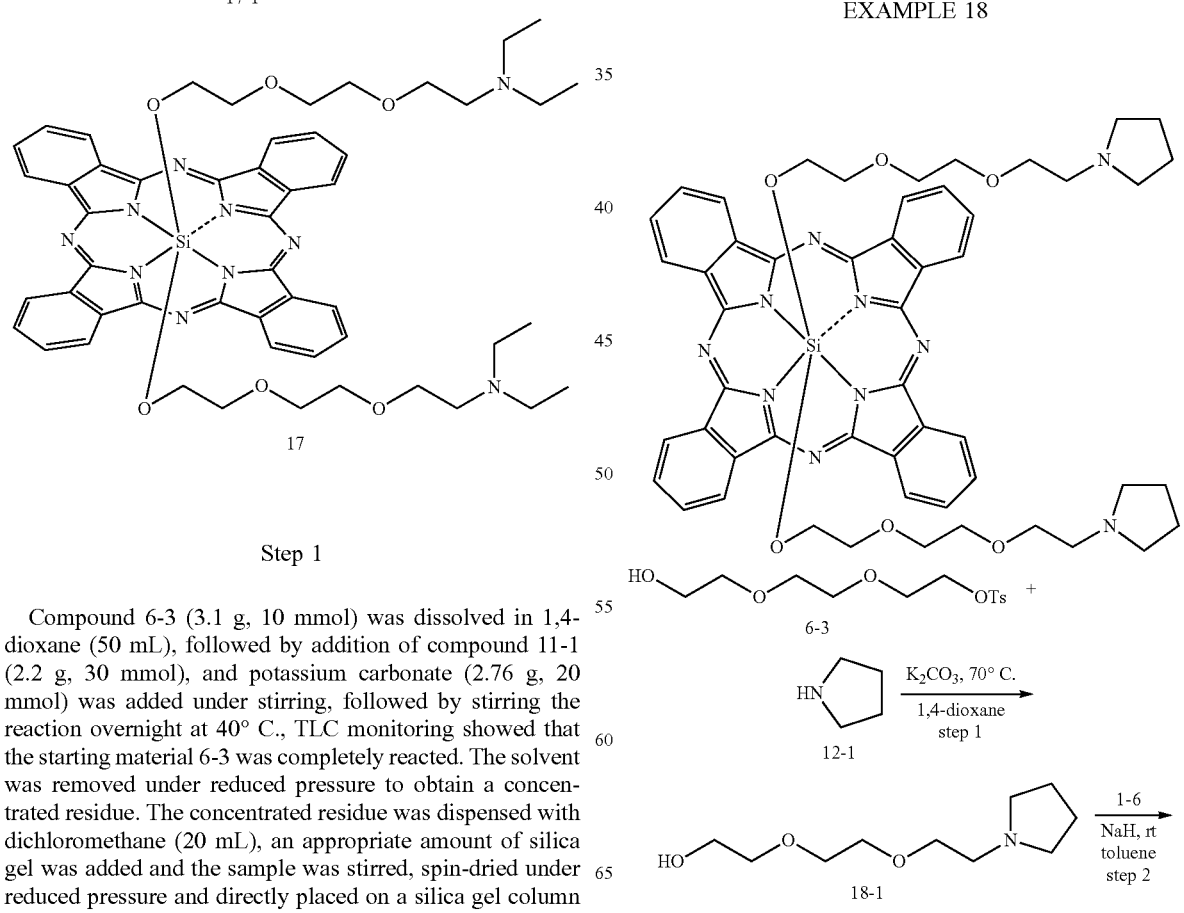

-continued

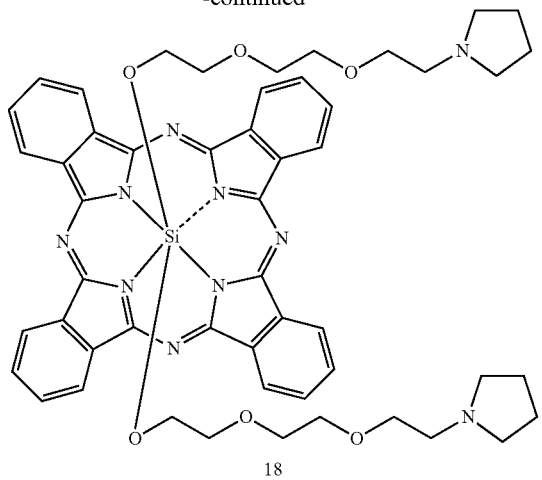

18

Step 1

Compound 6-3 (3.04 g, 10 mmol) was dissolved in 1,4-dioxane (50 mL), followed by addition of compound 12-1 (2.14 g, 30 mmol), and potassium carbonate (2.76 g, 20 mmol) was added under stirring, followed by stirring the reaction overnight at 40° C., TLC monitoring showed that the starting material 6-3 was completely reacted. The solvent was removed under reduced pressure to obtain a concentrated residue. The concentrated residue was dispensed with dichloromethane (20 mL), an appropriate amount of silica gel was added and the sample was stirred, spin-dried under reduced pressure and directly placed on a silica gel column for column chromatographic purification, with an eluent (dichloromethane:methanol=20/1-5/1) to obtain the target product 18-1 (0.92 g, 45.3%) as a pale yellow oil, LC-MS: m/z=204[M+H]$^+$.

Step 2

Compound 18-1 (203 mg, 1 mmol), compound 1-6 (305 mg, 0.5 mmol) and sodium hydride (80 mg, 2 mmol, 60% w/w) were added into a 100 mL reaction flask, then toluene (25 mL) was added to the reaction system. The atmosphere of the reaction system was changed to a nitrogen atmosphere using nitrogen ball and the reaction was performed at room temperature and monitored by TLC. After TLC showed that compound 1-6 was completely conversed, the reaction system was concentrated under reduced pressure, then 10 mL of water was added to the reaction system, and the resulting mixture was extracted three times with ethyl acetate (10 mL). The extract liquid was combined, washed with saturated brine, dried over anhydrous sodium sulfate, concentrated, and purified by silica gel column chromatography, with an eluent of ammoniated dichloromethane:methanol=100/3-50/1, to obtain the target product 18 (62 mg, 13.1%) as a deep blue solid. $^1$H NMR (500 MHz, CDCl$_3$): δ 9.63-9.61 (m, 8H), 8.34-8.32 (m, 8H), 2.94 (t, J=5 Hz, 4H), 2.41 (t, J=5 Hz, 4H), 2.26-2.23 (m, 8H), 1.65-1.62 (m, 16H), 0.38 (t, J=7.5 Hz, 4H), −1.99 (t, J=7.5 Hz, 4H). HRMS: 945.4230 [M+H]$^+$.

EXAMPLE 19

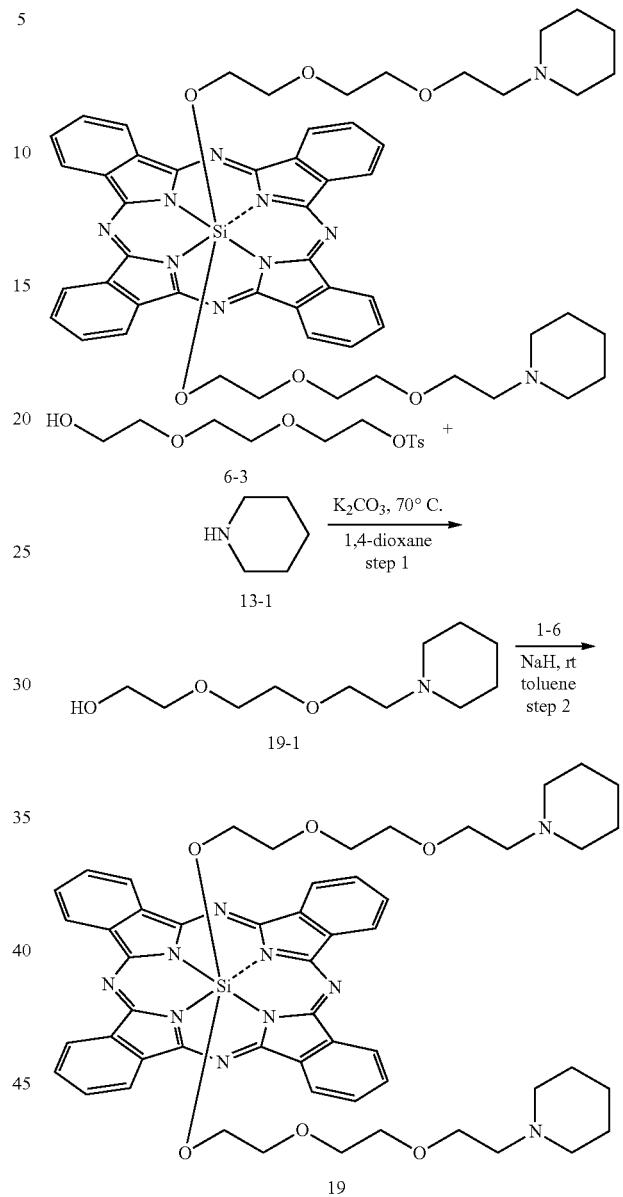

19

Step 1

Compound 6-3 (3.04 g, 10 mmol) was dissolved in 1,4-dioxane (50 mL), followed by addition of compound 13-1 (2.52 g, 30 mmol), and potassium carbonate (2.76 g, 20 mmol) was added under stirring, followed by stirring the reaction overnight at 40° C., TLC monitoring showed that the starting material 6-3 was completely reacted. The solvent was removed under reduced pressure to obtain a concentrated residue. The concentrated residue was dispensed with dichloromethane (20 mL), an appropriate amount of silica gel was added and the sample was stirred, spin-dried under reduced pressure and directly placed on a silica gel column for column chromatographic purification, with an eluent (dichloromethane:methanol=20/1-5/1) to obtain the target product 19-1 (0.72 g, 33.2%) as a pale yellow oil, LC-MS: m/z=218[M+H]⁺.

Step 2

Compound 19-1 (150 mg, 0.69 mmol), compound 1-6 (214 mg, 0.35 mmol) and sodium hydride (55 mg, 1.38 mmol, 60% w/w) were added into a 100 mL reaction flask, then toluene (20 mL) was added to the reaction system. The atmosphere of the reaction system was changed to a nitrogen atmosphere using nitrogen ball and the reaction was performed at room temperature and monitored by TLC. After TLC showed that compound 1-6 was completely conversed, the reaction system was concentrated under reduced pressure, then 10 mL of water was added to the reaction system, and the resulting mixture was extracted three times with ethyl acetate (10 mL). The extract liquid was combined, washed with saturated brine, dried over anhydrous sodium sulfate, concentrated, and purified by silica gel column chromatography, with an eluent of ammoniated dichloromethane:methanol=100/3-50/1, to obtain the target product 19 (115 mg, 33.8%) as a deep blue solid. ¹H NMR (500 MHz, CDCl₃): δ 9.63-9.61 (m, 8H), 8.34-8.32 (m, 8H), 2.94 (t, J=5 Hz, 4H), 2.39 (t, J=5 Hz, 4H), 2.12-2.09 (m, 8H), 1.63-1.61 (m, 8H), 1.42-1.38 (m, 12H), 0.39 (t, J=7.5 Hz, 4H), −1.90 (t, J=7.5 Hz, 4H); HRMS: 973.4539 [M+H]⁺.

EXAMPLE 20

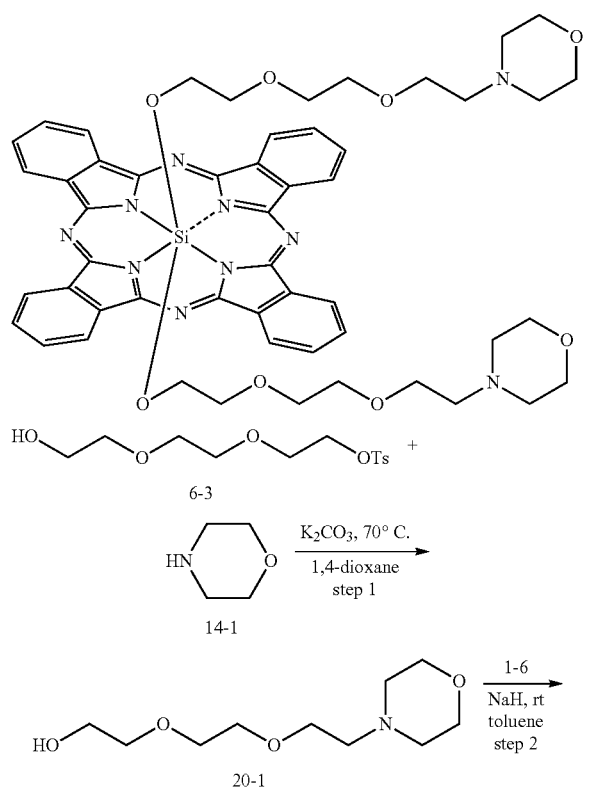

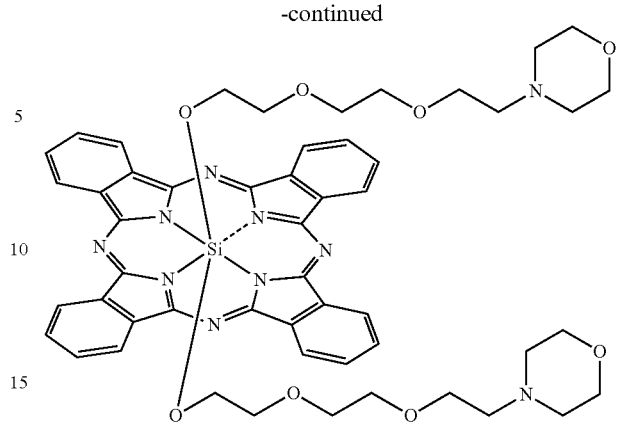

Step 1

Compound 6-3 (3.04 g, 10 mmol) was dissolved in 1,4-dioxane (50 mL), followed by addition of compound 14-1 (2.6 g, 30 mmol), and potassium carbonate (2.76 g, 20 mmol) was added under stirring, followed by stirring the reaction overnight at 40° C., TLC monitoring showed that the starting material 6-3 was completely reacted. The solvent was removed under reduced pressure to obtain a concentrated residue. The concentrated residue was dispensed with dichloromethane (20 mL), an appropriate amount of silica gel was added and the sample was stirred, spin-dried under reduced pressure and directly placed on a silica gel column for column chromatographic purification, with an eluent (dichloromethane:methanol=20/1-5/1) to obtain the target product 20-1 (0.75 g, 34.2%) as a pale yellow oil, LC-MS: m/z=220[M+H]⁺.

Step 2

Compound 20-1 (150 mg, 0.68 mmol), compound 1-6 (209 mg, 0.34 mmol) and sodium hydride (55 mg, 1.36 mmol, 60% w/w) were added into a 100 mL reaction flask, then toluene (20 mL) was added to the reaction system. The atmosphere of the reaction system was changed to a nitrogen atmosphere using nitrogen ball and the reaction was performed at room temperature and monitored by TLC. After TLC showed that compound 1-6 was completely conversed, the reaction system was concentrated under reduced pressure, then 10 mL of water was added to the reaction system, and the resulting mixture was extracted three times with ethyl acetate (10 mL). The extract liquid was combined, washed with saturated brine, dried over anhydrous sodium sulfate, concentrated, and purified by silica gel column chromatography, with an eluent of ammoniated dichloromethane:methanol=100/3-50/1, to obtain the target product 20 (57 mg, 15.7%) as a deep blue solid. ¹H NMR (500 MHz, CDCl₃): δ 9.63-9.62 (m, 8H), 8.35-8.32 (m, 8H), 3.51 (t, J=5 Hz, 8H), 2.90 (t, J=5 Hz, 4H), 2.40 (t, J=5 Hz, 4H), 2.19-2.12 (m, 12H), 1.64 (t, J=5 Hz, 4H), 0.39 (t, J=7.5 Hz, 4H), −1.92 (t, J=7.5 Hz, 4H); HRMS: 999.3946 [M+Na]⁺.

EXAMPLE 21

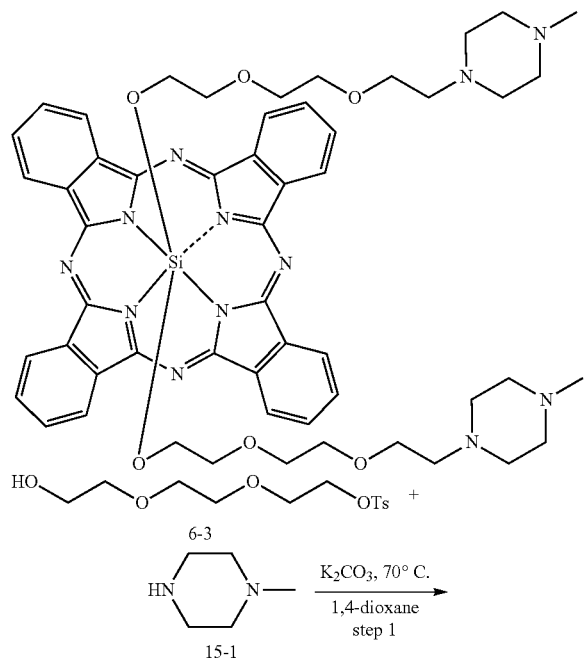

Step 1

Compound 6-3 (3.04 g, 10 mmol) was dissolved in 1,4-dioxane (50 mL), followed by addition of compound 15-1 (3 g, 30 mmol), and potassium carbonate (2.76 g, 20 mmol) was added under stirring, followed by stirring the reaction overnight at 40° C., TLC monitoring showed that the starting material 6-3 was completely reacted. The solvent was removed under reduced pressure to obtain a concentrated residue. The concentrated residue was dispensed with dichloromethane (20 mL), an appropriate amount of silica gel was added and the sample was stirred, spin-dried under reduced pressure and directly placed on a silica gel column for column chromatographic purification, with an eluent (dichloromethane:methanol=20/1-5/1) to obtain the target product 21-1 (1.45 g, 62.5%) as a pale yellow oil, LC-MS: m/z=233[M+H]$^+$.

Step 2

Compound 21-1 (200 mg, 0.86 mmol), compound 1-6 (263 mg, 0.43 mmol) and sodium hydride (69 mg, 1.72 mmol, 60% w/w) were added into a 100 mL reaction flask, then toluene (20 mL) was added to the reaction system. The atmosphere of the reaction system was changed to a nitrogen atmosphere using nitrogen ball and the reaction was performed at room temperature and monitored by TLC. After TLC showed that compound 1-6 was completely conversed, the reaction system was concentrated under reduced pressure, then 10 mL of water was added to the reaction system, and the resulting mixture was extracted three times with ethyl acetate (10 mL). The extract liquid was combined, washed with saturated brine, dried over anhydrous sodium sulfate, concentrated, and purified by silica gel column chromatography, with an eluent of ammoniated dichloromethane:methanol=100/3-50/1, to obtain the target product 21 (81 mg, 18.8%) as a deep blue solid. $^1$H NMR (500 MHz, CDCl$_3$): δ 9.63-9.62 (m, 8H), 8.34-8.33 (m, 8H), 2.91 (t, J=5 Hz, 4H), 2.39 (t, J=5 Hz, 4H), 2.28-2.20 (m, 14H), 2.14 (t, J=5 Hz, 4H), 1.68-1.60 (m, 12H), 0.39 (t, J=7.5 Hz, 4H), −1.92 (t, 4H, J=7.5 Hz); HRMS: 1003.4758 [M+H]$^+$.

EXAMPLE 22

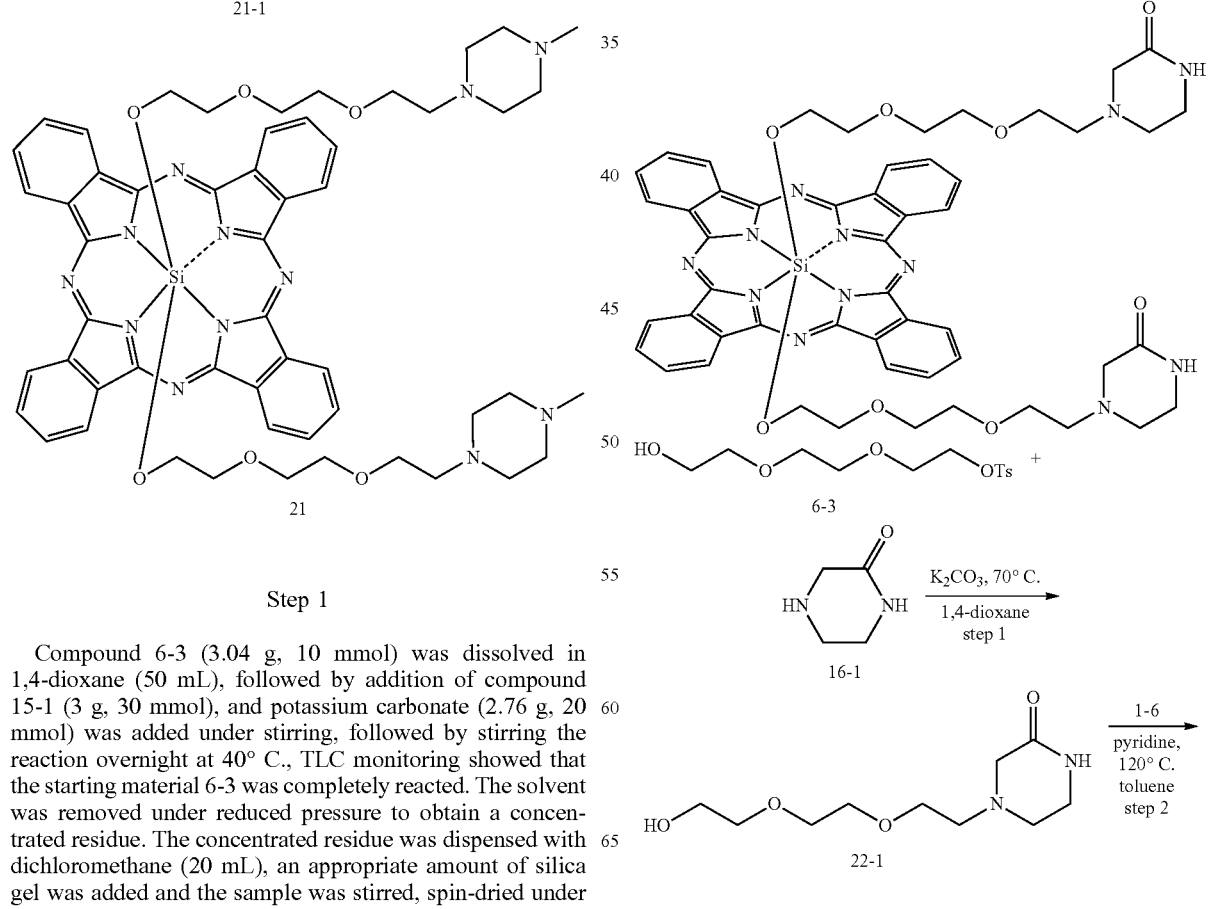

63

-continued

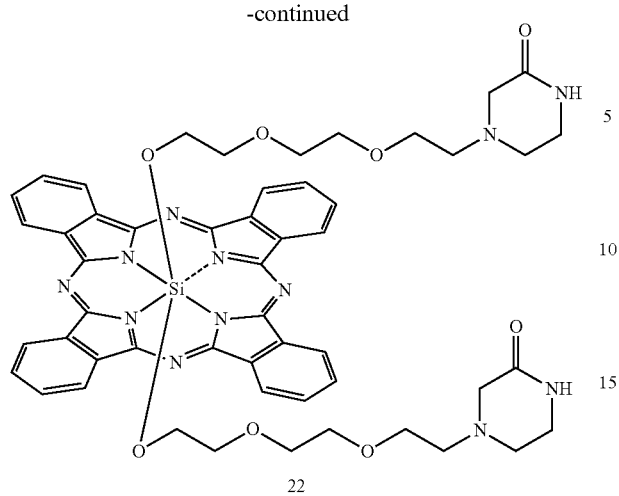

22

Step 1

Compound 6-3 (3.04 g, 10 mmol) was dissolved in 1,4-dioxane (50 mL), followed by addition of compound 16-1 (1 g, 10 mmol), and under stirring potassium carbonate (1.4 g, 10 mmol) was added, followed by stirring the reaction overnight at 70° C., TLC monitoring showed that the starting material 6-3 was completely reacted. The solvent was removed under reduced pressure to obtain a concentrated residue. The concentrated residue was dispensed with dichloromethane (20 mL), an appropriate amount of silica gel was added and the sample was stirred, spin-dried under reduced pressure and directly placed on a silica gel column for column chromatographic purification, with an eluent (dichloromethane:methanol=20/1-5/1) to obtain the target product 22-1 (1.1 g, 47.4%) as a pale yellow oil, LC-MS: m/z=233[M+H]$^+$.

Step 2

Compound 22-1 (100 mg, 0.43 mmol), compound 1-6 (128 mg, 0.21 mmol) and 0.5 mL of pyridine were added into a 100 mL reaction flask, then toluene (20 mL) was added to the reaction system. The atmosphere of the reaction system was changed to a nitrogen atmosphere using nitrogen ball, the temperature was heated to 120° C., and the reaction was performed at 120° C. for 4 hours. The reaction system was cooled to room temperature, concentrated under reduced pressure, then 10 mL of water was added to the reaction system, and the resulting mixture was extracted three times with ethyl acetate (10 mL). The extract liquid was combined, washed with saturated brine, dried over anhydrous sodium sulfate, concentrated, and purified by silica gel column chromatography, with an eluent of ammoniated dichloromethane:methanol=100/3-50/1, to obtain the target product 22 (52 mg, 24.7%) as a deep blue solid. $^1$H NMR (500 MHz, CDCl$_3$): δ 9.63-9.62 (m, 8H), 8.35-8.34 (m, 8H), 6.82-6.78 (m, 2H), 3.01-2.87 (m, 12H), 2.40 (t, J=5 Hz, 4H), 2.31 (t, J=5 Hz, 4H), 2.18 (t, J=5 Hz, 4H), 1.66 (t, J=5 Hz, 4H), 0.39 (t, J=7.5 Hz, 4H), −1.93 (t, J=7.5 Hz, 4H); HRMS: 1025.3847 [M+Na]$^+$.

64

EXAMPLE 23

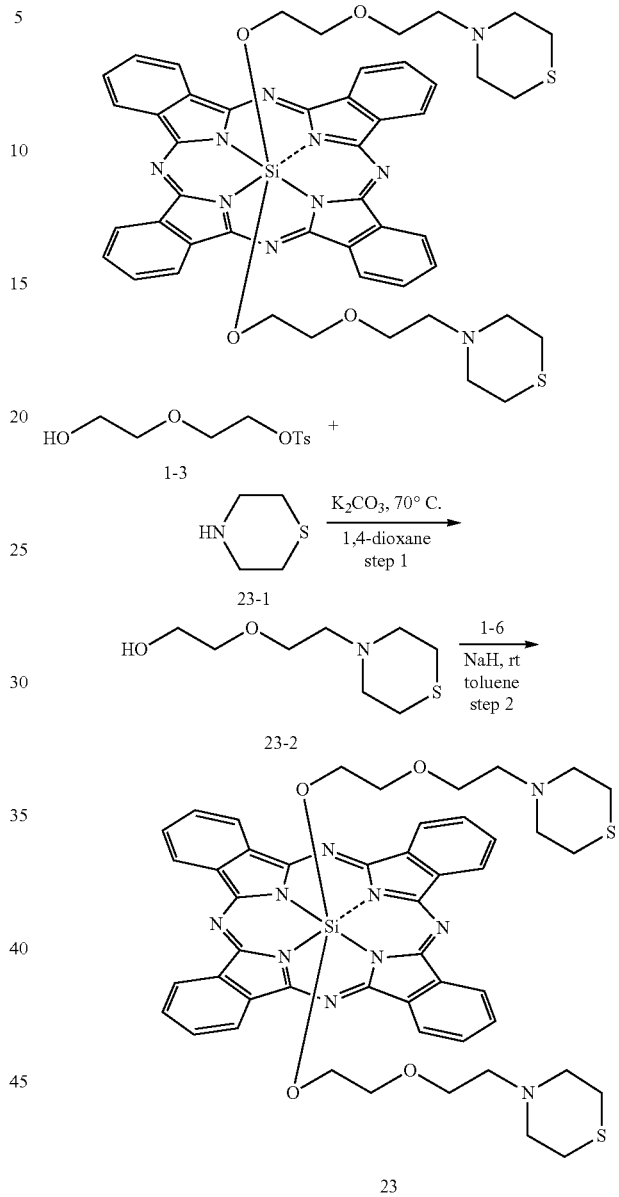

Step 1

Compound 1-3 (3.12 g, 12 mmol) was dissolved in 1,4-dioxane (50 mL), followed by addition of compound 23-1 (1 g, 10 mmol), and under stirring potassium carbonate (1.65 g, 12 mmol) was added, followed by stirring the reaction overnight at 70° C., TLC monitoring showed the starting material 1-3 was completely reacted. The solvent was removed under reduced pressure to obtain a concentrated residue. The concentrated residue was dispensed with dichloromethane (20 mL), an appropriate amount of silica gel was added and the sample was stirred, spin-dried under reduced pressure and directly placed on a silica gel column for column chromatographic purification, with an eluent (dichloromethane:methanol=20/1-5/1) to obtain the target product 23-2 (1.2 g, 62.8%) as a pale yellow oil, LC-MS: m/z=192[M+H]$^+$.

Step 2

Compound 23-2 (100 mg, 0.52 mmol), compound 1-6 (160 mg, 0.26 mmol) and sodium hydride (42 mg, 1.04 mmol, 60% w/w) were added into a 100 mL reaction flask, then toluene (20 mL) was added to the reaction system. The atmosphere of the reaction system was changed to a nitrogen atmosphere using nitrogen ball and the reaction was performed at room temperature and monitored by TLC. After TLC showed that compound 1-6 was completely conversed, the reaction system was concentrated under reduced pressure, then 10 mL of water was added to the reaction system, and the resulting mixture was extracted three times with ethyl acetate (10 mL). The extract liquid was combined, washed with saturated brine, dried over anhydrous sodium sulfate, concentrated, and purified by silica gel column chromatography, with an eluent of ammoniated dichloromethane:methanol=100/3-50/1, to obtain the target product 23 (140 mg, 59%) as a deep blue solid. $^1$H NMR (500 MHz, CDCl$_3$): δ 9.64-9.62 (m, 8H), 8.36-8.34 (m, 8H), 2.32-2.29 (m, 8H), 1.99-1.97 (m, 8H), 1.54 (t, J=5 Hz, 4H), 1.38 (t, J=7.5 Hz, 4H), 0.38 (t, J=5 Hz, 4H), −1.93 (t, J=5 Hz, 4H); HRMS: 943.2963 [M+Na]$^+$.

EXAMPLE 24

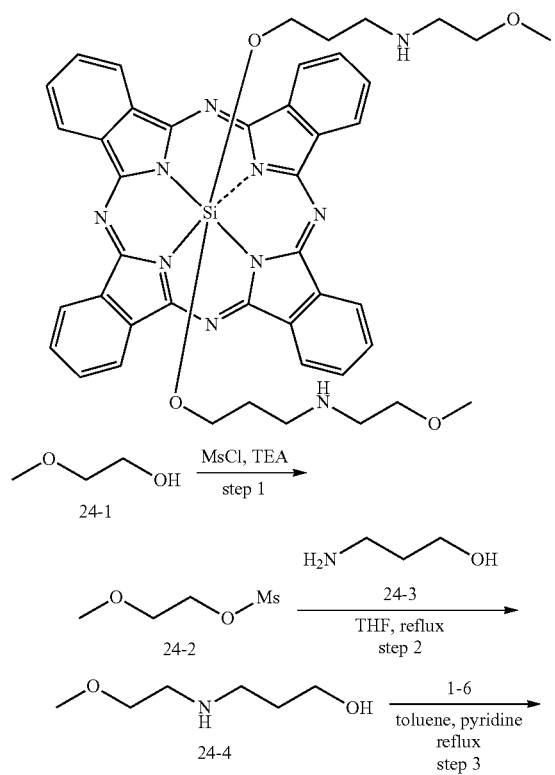

Step 1

7.6 g (0.1 mol) of ethylene glycol monomethyl ether 24-1 was dissolved in 150 mL of anhydrous dichloromethane, 20 g of triethylamine was added, 0.1 M of a solution of methanesulfonyl chloride (0.11 mol) in dichloromethane was added dropwise at 0° C. After the addition was complete, the mixture was reacted at room temperature overnight, washed with water, dried and concentrated to obtain 14.9 g of ethylene glycol monomethyl ether protected with Ms 24-2, yield 97%.

Step 2

1.54 g of ethylene glycol monomethyl ether protected with Ms 24-2 (0.01 mol) and 7.5 g of amino-n-propanol 24-3 (0.1 mol) was dissolved in 30 mL of anhydrous tetrahydrofuran, and the mixture was reacted under refluxing for 8 hours. The reaction solution was washed with water and concentrated to obtain the crude target product 24-4. The crude product was dissolved in dichloromethane (30 mL), an appropriate amount of silica gel was added and the sample was stirred, spin-dried under reduced pressure and directly placed on a silica gel column for column chromatographic purification, with an eluent solution (dichloromethane:methanol=20/1-5/1) to obtain 0.63 g of the target product 24-4 as a pale yellow liquid, yield 47%. LC-MS: m/z=134 [M+H]+.

Step 3

122 mg of silicon phthalocyanine dichloride 1-6 (0.02 mmol) and 266 mg of compound 24-4 (2 mmol) was dissolved in 15 mL of anhydrous toluene and 0.5 mL of pyridine, and the mixture was reacted under refluxing away from light under N2 for 6 hours. The reaction solution was washed with water (100 mL) three times, dried, concentrated, and purified by silica gel column chromatography, with an eluent of ammoniated dichloromethane:methanol=100/3-50/1, to obtain 57 mg of the target product 24, yield 33%. $^1$H NMR: 9.63 (m, 8 H, ArH), 8.34 (m, 8 H, ArH), 2.98 (s, s, 6 H, CH$_3$), 2.64 (m, 4 H, CH$_2$), 1.50 (m, 4 H, CH$_2$), −0.10 (m, 4 H, CH$_2$), −1.34 (m, 4 H, CH$_2$), −2.05 (m, 4 H, CH$_2$). HRMS: [M+2H]$^{2+}$: 806.3462.

EXAMPLE 25

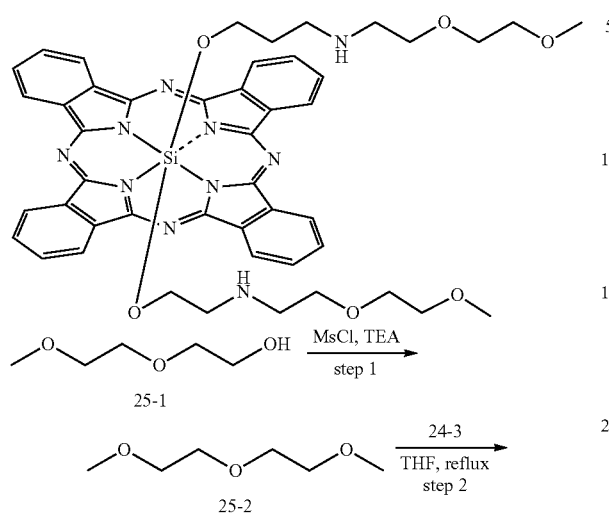

Step 1

12.0 g (0.1 mol) of diethylene glycol monomethyl ether 25-1 was dissolved in 150 mL of anhydrous dichloromethane, 20 g of triethylamine was added, 0.1 M of a solution of methanesulfonyl chloride (0.11 mol) in dichloromethane was added dropwise at 0° C. After the addition was complete, the mixture was reacted at room temperature overnight, washed with water, dried and concentrated to obtain 18.3 g of diethylene glycol monomethyl ether protected with Ms 25-2, yield 92%.

Step 2

1.98 g of diethylene glycol monomethyl ether protected with Ms 25-2 (0.01 mol) and 7.5 g of amino-n-propanol 24-3 (0.1 mol) was dissolved in 30 mL of anhydrous tetrahydrofuran, and the mixture was reacted under refluxing for 6 hours. The reaction solution was washed with water and concentrated to obtain the crude target product 25-3. The crude product was dissolved in dichloromethane (20 mL), an appropriate amount of silica gel was added and the sample was stirred, spin-dried under reduced pressure and directly placed on a silica gel column for column chromatographic purification, with an eluent solution (dichloromethane:methanol=20/1-5/1) to obtain 1.23 g of the target product 25-3 as a pale yellow liquid, yield 70%. LC-MS: m/z=178 [M+H]$^+$.

Step 3

61 mg of silicon phthalocyanine dichloride 1-6 (0.01 mmol) and 177 mg of the compound 25-3 (1 mmol) was dissolved in 12 mL of anhydrous toluene and 0.5 mL of pyridine, and the mixture was reacted under refluxing away from light under N2 for 6 hours. The reaction solution was washed with water (100 mL) three times, dried, concentrated, and purified by silica gel column chromatography, with an eluent of ammoniated dichloromethane:methanol=100/3-50/1, to obtain 51 mg of the target product 25, yield 57%. $^1$H NMR: 9.72 (m, 8 H, ArH), 8.49 (m, 8 H, ArH), 3.23 (m, 4 H, CH$_2$), 3.18 (m, 4 H, CH$_2$), 3.11 (s, 6 H, CH$_3$), 2.70 (m, 4 H, CH$_2$), 1.51 (m, 4 H, CH$_2$), −0.15 (m, 4 H, CH$_2$), −1.36 (m, 4 H, CH$_2$), −1.98 (m, 4 H, CH$_2$). HRMS: [M+H]$^+$: 893.3920.

EXAMPLE 26

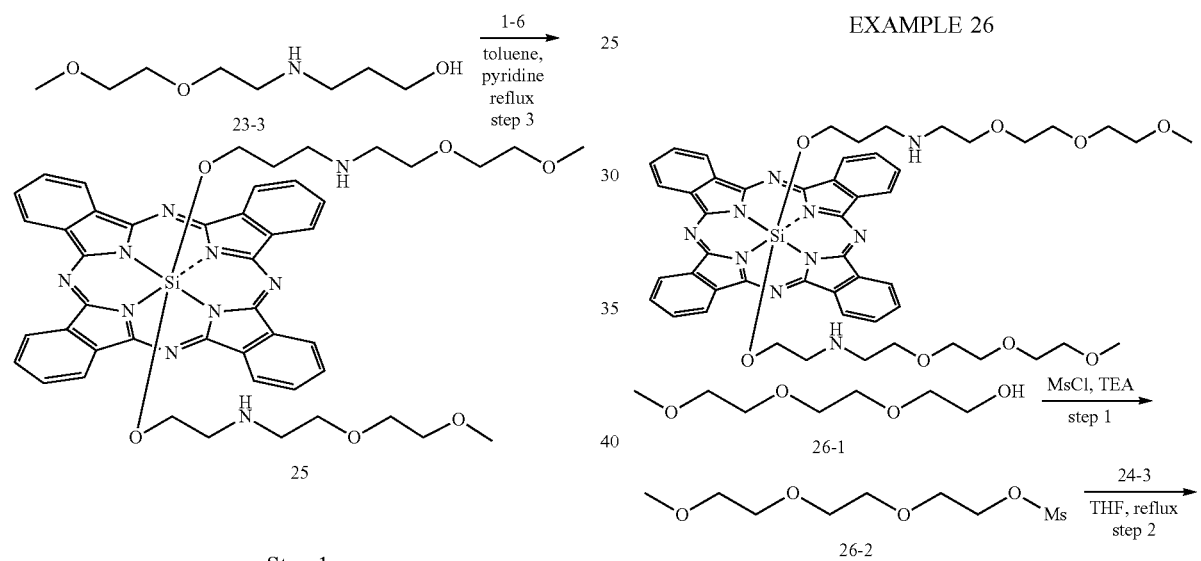

Step 1

16.4 g (0.1 mol) of triethylene glycol monomethyl ether 26-1 was dissolved in 150 mL of anhydrous dichloromethane, 20 g of triethylamine was added, 0.1 M of a solution of methanesulfonyl chloride (0.11 mol) in dichloromethane was added dropwise at 0° C. After the addition was complete, the mixture was reacted at room temperature overnight, washed with water, dried and concentrated to obtain 21.9 g of triethylene glycol monomethyl ether protected with Ms 26-2, yield 91%.

Step 2

2.44 g of triethylene glycol monomethyl ether protected with Ms 26-2 (0.01 mol) and 7.5 g of amino-n-propanol 24-3 (0.1 mol) was dissolved in 30 mL of anhydrous tetrahydrofuran, and the mixture was reacted under refluxing for 6 hours. The reaction solution was washed with water and concentrated to obtain the crude target product 26-3. The crude product was dissolved in dichloromethane (20 mL), an appropriate amount of silica gel was added and the sample was stirred, spin-dried under reduced pressure and directly placed on a silica gel column for column chromatographic purification, with an eluent solution (dichloromethane:methanol=20/1-5/1) to obtain 1.45 g of the target product 26-3 as a pale yellow liquid, yield 66%. LC-MS: m/z=222 [M+H]$^+$.

Step 3

61 mg of silicon phthalocyanine dichloride 1-6 (0.01 mmol) and 221 mg of the compound 26-3 (1 mmol) was dissolved in 12 mL of anhydrous toluene and 0.5 mL of pyridine, and the mixture was reacted under refluxing away from light under N2 for 6 hours. The reaction solution was washed with water (100 mL) three times, dried, concentrated, and purified by silica gel column chromatography, with an eluent of ammoniated dichloromethane:methanol=100/3-50/1, to obtain 61 mg of the target product 26, yield 62%. The purity was more than 95%. $^1$H NMR: 9.66 (m, 8 H, ArH), 8.41 (m, 8 H, ArH), 3.03 (m, 4 H, CH$_2$), 3.02 (m, 4 H, CH$_2$), 2.99 (m, 4 H, CH$_2$), 2.98 (m, 4 H, CH$_2$), 2.97 (m, 4 H, CH$_2$), 2.79 (s, s, 6 H, CH$_3$), 0.88 (m, 4 H, CH$_2$), 0.19 (m, 4 H, CH$_2$), −0.87 (m, 4 H, CH$_2$), −2.02 (m, 4 H, CH$_2$). HRMS: [M+H]$^+$: 981.4451.

Test example: in vitro tumor experiment

Test samples: compounds 1-26 of the present invention

Positive Control: hematoporphyrin injection (trade name: Hiporfin, Chongqing Huading modern biopharmaceutical Ltd. Co.).

Main Reagent

DMSO was purchased from the MP Company (U.S.A.); polyoxyethylene castor oil was purchased from the Sigma Company.

Dose Design and Group 26 test samples were designed and divided into 5-10 doses, with each dose concentration being distributed between 5000-0.025 ng/mL (final concentration of the sample after being added into cell well); at the same time the negative control group (a solvent containing no test sample) was given, a blank well without cell suspension only with complete culture medium was also given. Each 96-well plate does not have the positive control group. Positive drug (Hiporfin) was treated according to the test samples (at a dose of 10, 5, 2.5, 1.25, 0.625 µg/mL).

Experimental Method

1. Preparation Method of Main Reagent 1.1. RPMI-1640 complete culture medium: to 500 mL RPMI-1640 liquid medium (GIBCO Company), 100,000 units of penicillin/streptomycin and 56 mL of fetal bovine serum were added and mixed uniformly.

1.2. DMEM complete culture medium: to 500 mL DMEM liquid medium (GIBCO Company), 100,000 units of penicillin/streptomycin and 56 mL of fetal bovine serum were added and mixed uniformly.

1.3. MTT solution (MTT: 3-(4,5-dimethylthiazol-2-yl)-2,5-diphenyl tetrazolium bromide, purchased from the MP Company (U.S.A.)): the powdered MTT was dissolved into a PBS solution at a concentration of 5 mg/mL, filtered and sterilized, and it was formulated when used.

2. Preparation Method of Test Sample:

The test sample was formulated into a mother liquor at a concentration of 1 mM with DMSO; 100 µL of 1 mg/mL of the mother liquor was taken in the experiment, 1.15 mL 0.5% (w/w) polyoxyethylenated castor oil in pH 7.4 PBS buffer was added to prepare a 80 µg/mL drug liquid, which was diluted into different concentrations with a culture medium. For each test sample and the negative control group, the final concentration of DMSO was ≤1%. A 5 mL liquid solution containing 25 mg of Hiporfin was formulated, and the concentration was 5 mg/mL. 100 µL of 5 mg/mL of the Hiporfin preparation was taken, 4.90 mL of the pH 7.4 PBS buffer was added to prepare a 100 µg/mL drug liquid, which was diluted into different concentrations with a culture medium.

3. Cell culture: human melanoma cell A375 (Cell bank of Yat-sen University) and human esophageal cancer cell Te-1 (Cell Bank of the Chinese academy of sciences, Shanghai) were each cultured in 10% FBS-containing DMEM medium in a incubator with 37° C., 5% CO$_2$, and passaged after digestion with 0.25% trypsin. Cells in logarithmic growth phase were collected for experiments.

4. MTT Experimental Method:

Adherent tumor cells in logarithmic growth phase were selected and digested with trypsin, then formulated into a suitable concentration of cell suspensions with a RPMI 1640 or DMEM medium containing 10% fetal bovine serums and inoculated in a 96-well culture plate. Each well was inoculated with 100 µL, after the addition was completed in each row, cell suspension was shaken. After the addition of cells was complete, the culture plate was rotated lightly and horizontally such that the cells were uniformly dispersed on the surface of the plate wells, a circle of wells around the 96-hole plate was added with a sterile PBS, and incubated under conditions of 37° C., 5% CO$_2$ for 24 h. Then, 100 µL of different concentrations of test drugs, positive drugs, solvents and culture mediums were added respectively, with three parallel wells in each group. After mixing uniformly, they were divided into two groups, a light group and a dark group, and both were administered with drugs and co-cultured for 2 h, then the medium was discarded and the DMEM complete medium containing no test sample was re-added. The plate was placed under conditions of 37° C., 5% CO$_2$ for another 24 h. After 24 h, each well was added with 5 mg/mL MTT, 20 µL, and incubated under conditions of 37° C., 5% CO$_2$ for 4 h, the supernatant was carefully sucked and discarded; each well was added with 200 µL DMSO, shaken for 10 min, so that the formazan particles formed were fully dissolved, then the absorbance value was determined by a microplate reader, with the detection wavelength of 570 nm, and the reference wavelength of 630 nm. The above experiment was repeated 3 times, the average IC$_{50}$ value of the 3 experiments was obtained as the final index. The light source was provided by a 200 watt halogen lamp connected to an insulated water tank plus a filter of more than 610 nm, and the light dose was 48 J cm$^{-2}$.

Calculation Method of Growth Inhibition Rate of Drug on Tumor Cell:

Tumor cell growth inhibition rate (%)=[(OD mean value of the negative control group−OD mean value of the drug group)/OD mean value of the negative control group]× 100%. The calculation of half inhibitory concentration $IC_{50}$ was determined by logit regression method.

Experimental results:

| Compound No. | Skin cancer A375 Light $IC_{50}$ ng/mL | skin cancer A375 Dark $IC_{50}$ ng/mL | Esophagus carcinomas Te-1 Light $IC_{50}$ ng/mL | Esophagus carcinomas Te-1 Dark $IC_{50}$ ng/mL |
|---|---|---|---|---|
| 1 | 11 | >250 | 1.8 | >5000 |
| 2 | 2 | >250 | 0.07 | 4000 |
| 3 | 1.8 | >250 | <0.025 | 5000 |
| 4 | 2.4 | >250 | <0.025 | 3750 |
| 5 | 1.6 | >250 | <0.025 | >5000 |
| 6 | 9 | >250 | 10 | >5000 |
| 7 | 9 | >250 | 17 | >5000 |
| 8 | 1.9 | >250 | <0.025 | >5000 |
| 9 | 12 | >250 | 4 | >5000 |
| 10 | 1.7 | >250 | <0.025 | >5000 |
| 11 | 1 | >250 | 0.03 | 3150 |
| 12 | 1.8 | >250 | 2.5 | >5000 |
| 13 | 13 | >5000 | 1.5 | >5000 |
| 14 | 8 | >5000 | <0.025 | >5000 |
| 15 | 1.7 | 4500 | <0.025 | >5000 |
| 16 | 1.6 | >5000 | <0.025 | >5000 |
| 17 | 0.8 | 1560 | <0.025 | 1530 |
| 18 | 0.2 | 1890 | <0.025 | 2052 |
| 19 | 0.1 | >5000 | <0.025 | >5000 |
| 20 | 0.1 | >5000 | <0.025 | >5000 |
| 21 | 1.2 | 3025 | <0.025 | >5000 |
| 22 | 12 | >5000 | 18 | >5000 |
| 23 | 1.8 | >5000 | 2.1 | >5000 |
| 24 | 1.5 | >5000 | 11 | >5000 |
| 25 | 16 | >5000 | 12.7 | >5000 |
| 26 | 12.4 | >5000 | 14.6 | >5000 |
| Hiporfin | 2000 | >10000 | 5000 | >10000 |

It can be seen from the above test results that China's only marketed anticancer photosensitizer Hiporfin had an $IC_{50}$ value of 2000 ng/mL with respect to skin cancer A375 cancer cells under light illumination and an $IC_{50}$ value of 5000 ng/mL with respect to the esophageal cancer Te-1 cancer cells under light illumination. The optical activity of the compounds 1-26 disclosed in the present invention is much higher than that of the marketed control drug Hiporfin: for skin cancer A375 cells and esophageal cancer Te-1 cancer cells under the same light illumination conditions, in both cases the $IC_{50}$ values were less than 18 ng/mL, the $IC_{50}$ values of some of the compounds were even less than 0.025 ng/mL, and the in vitro photodynamic activity thereof was as 200000 times as that of the drug already marketed. It is also noted that the $IC_{50}$ values of these compounds, under dark condition, are more than 5000 ng/mL, and the $IC_{50}$ values thereof on tumor cells under dark condition is as 200000 times as the $IC_{50}$ values under light illumination condition, indicating that theses compounds have very low dark toxicity and a very wide safety window. In summary, the series of compounds disclosed in the present invention have very low dark toxicity and very high photodynamic activity, is a potential second-generation of photosensitive drug having high efficiency and low toxicity.

What is claimed is:

1. A compound of formula (I):

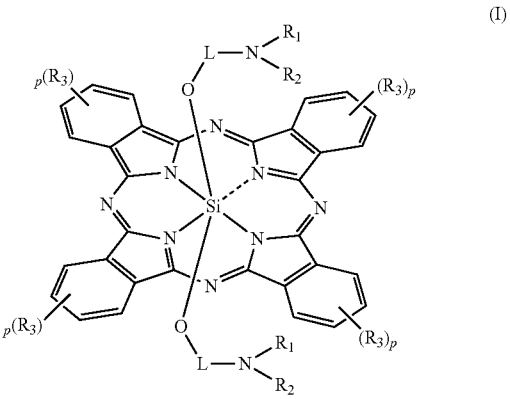

or a tautomer, mesomer, racemate, enantiomer, diastereoisomer thereof, or mixture thereof, or a pharmaceutically acceptable salt thereof, wherein:

L is —$CH_2$—$CH_2$—O—$CH_2$—$CH_2$—, wherein one or more hydrogens are optionally substituted by a group selected from the group consisting of $C_{1-4}$alkyl, halo$C_{1-4}$ alkyl, $C_{1-4}$alkoxy, halo$C_{1-4}$alkoxy, halogen, amino, nitro, hydroxyl and cyano;

$R_1$ selected from the group consisting of a hydrogen atom and —$C_{1-4}$alkylene-O—$C_{1-4}$alkyl, wherein said $C_{1-4}$alkyl and $C_{1-4}$alkylene are optionally substituted by one or more groups selected from the group consisting of $C_{1-4}$alkyl, halo$C_{1-4}$alkyl, $C_{1-4}$alkoxy, halo$C_{1-4}$ alkoxy,halogen,amino, nitro, hydroxyl and cyano;

$R_1$ is selected from the group consisting of $C_{1-4}$alkyl and —$C_{1-4}$alkylene-O—$C_{1-4}$alky, wherein said $C_{1-4}$alkyl and $C_{1-4}$alkylene are optionally substituted by one or more groups selected from the group consisting of $C_{1-4}$alkyl, halo$C_{1-4}$alkyl, $C_{1-4}$alkoxy, halo$C_{1-4}$alkoxy, halogen, amino, nitro, hydroxyl and cyano; or $R_1$ and $R_2$ together with the atoms to which they are attached form a following group:

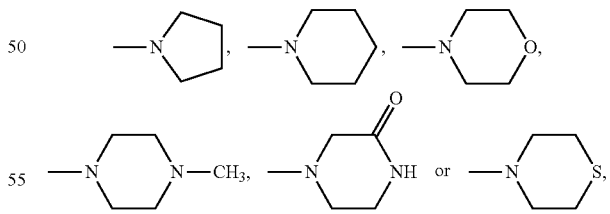

said group is optionally substituted by one or more groups selected from the group consisting of $C_{1-4}$alkyl, halo$C_{1-4}$alkyl, $C_{1-4}$alkoxy, halo$C_{1-4}$alkoxy, halogen, amino, nitro, hydroxyl and cyano;

$R_3$ are the same or different and are each independently selected from the group consisting of a hydrogen atom, $C_{1-4}$alkyl, halo$C_{1-4}$alkyl, $C_{1-4}$alkoxy, halo$C_{1-4}$alkoxy, halogen, amino, nitro, hydroxyl and cyano, and p is an integer of 0, 1, 2, 3 or 4.

2. A compound of formula (I):

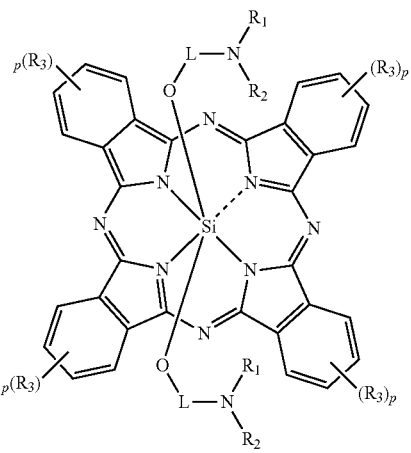

or a tautomer, mesomer, racemate, enantiomer, diastereoisomer thereof, or mixture thereof, or a pharmaceutically acceptable salt thereof,
wherein:
L is —$CH_2$—$CH_2$—O—$CH_2$—$CH_2$—O—$CH_2$—$CH_2$—, wherein one or more hydrogens are optionally substituted by a group selected from the group consisting of $C_{1-4}$alkyl, halo$C_{1-4}$alkyl, $C_{1-4}$alkoxy, halo$C_{1-4}$alkoxy, halogen, amino, nitro, hydroxyl and cyano;

$R_1$ and $R_2$ are each independently selected from the group consisting of a hydrogen atom, $C_{1-4}$alkyl and —$C_{1-4}$alkylene-O—$C_{1-4}$alky, wherein said $C_{1-4}$alkyl and $C_{1-4}$alkylene are optionally substituted by one or more groups selected from the group consisting of $C_{1-4}$alkyl, halo$C_{1-4}$alkyl, $C_{1-4}$alkoxy, halo$C_{1-4}$alkoxy, halogen, amino, nitro, hydroxyl and cyano; or $R_1$ and $R_2$ together with the atoms to which they are attached form a following group:

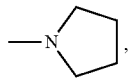

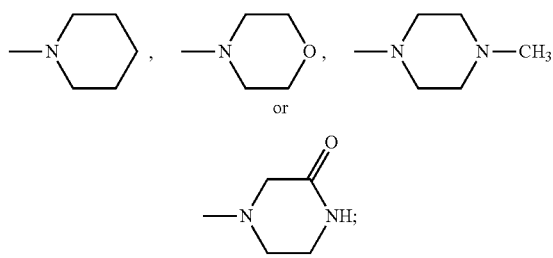

$R_3$ are the same or different and are each independently selected from the group consisting of a hydrogen atom, $C_{1-4}$alkyl, halo$C_{1-4}$alkyl, $C_{1-4}$alkoxy, halo$C_{1-4}$alkoxy, halogen, amino, nitro, hydroxyl and cyano, and
p is an integer of 0, 1, 2, 3 or 4.

3. The compound of formula (I) according to claims 1 or 2, wherein $R_3$ is a hydrogen atom.

4. The compound of formula (I) according to claims 1 or 2, wherein p is 0.

5. The compound of formula (I) according to claim 1, wherein:
L is —$CH_2$—$CH_2$—O—$CH_2$—$CH_2$; and
$R_1$ is selected from the group consisting of a hydrogen atom and —$CH_2$—$CH_2$—O—$CH_3$;
$R_2$ is selected from the group consisting of $C_{1-4}$alkyl, —$CH_2$—$CH_2$—O—$CH_3$ and —$CH_2$—$CH_2$—$CH_2$—O—$CH_3$; or
$R_1$ and $R_2$ together with the atoms to which they are attached form a following group:

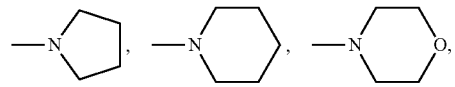

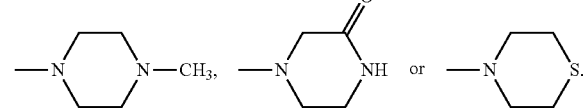

6. The compound of formula (I) according to claim 2, wherein:
L is —$CH_2$—$CH_2$—O—$CH_2$—$CH_2$—O—$CH_2$—$CH_2$—; and
$R_1$ and $R_2$ are each independently selected from the group consisting of the group consisting of a hydrogen atom, $C_{1-4}$alkyl, —$CH_2$—$CH_2$—O—$CH_3$ and —$CH_2$—$CH_2$—$CH_2$—O—$CH_3$; or
$R_1$ and $R_2$ together with the atoms to which they are attached form a following group:

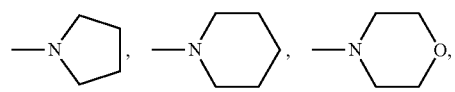

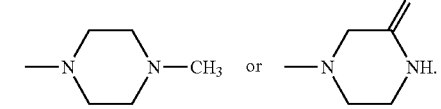

7. A compound selected from the group consisting of:

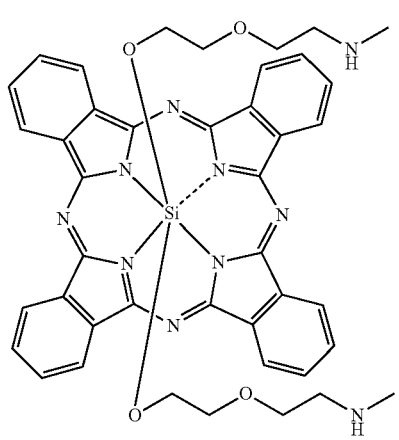

75
-continued
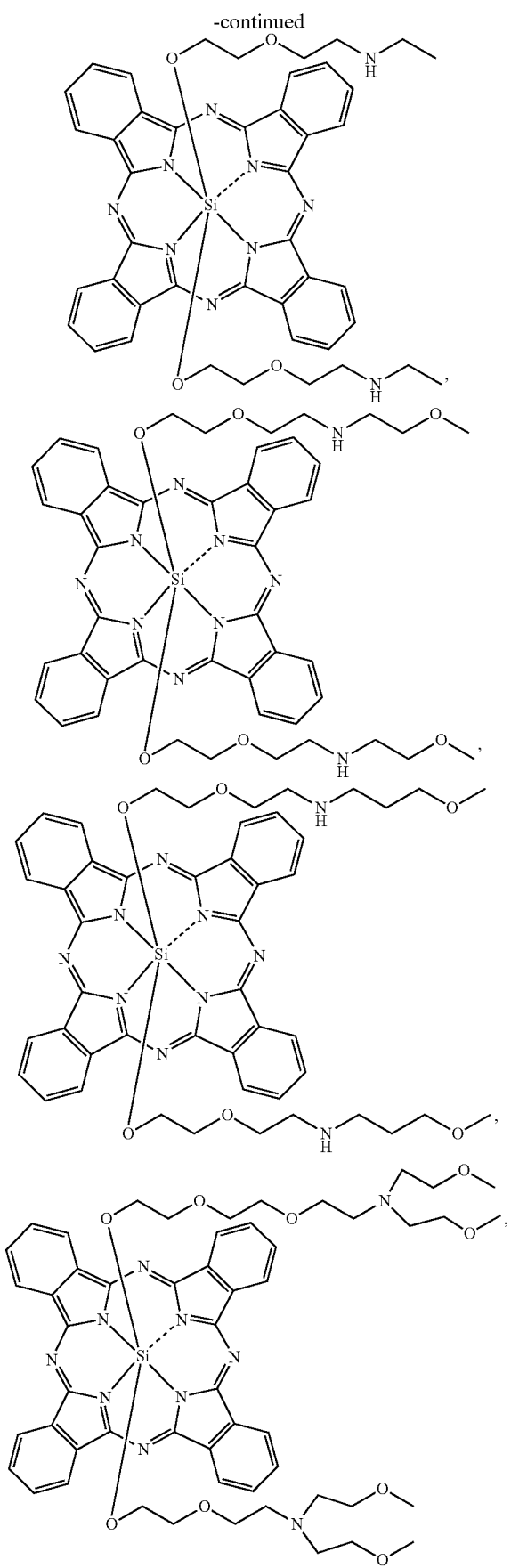
76
-continued
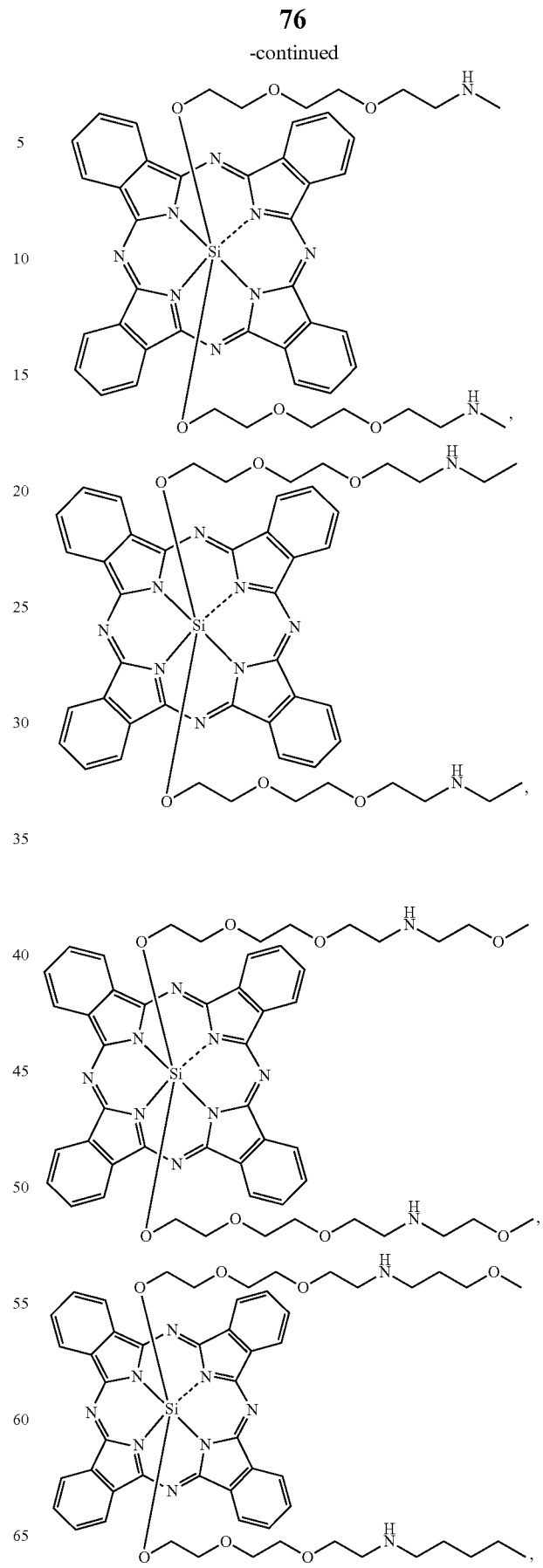

77
-continued
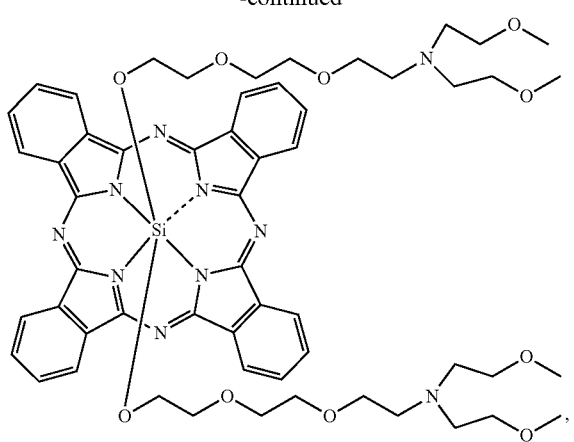
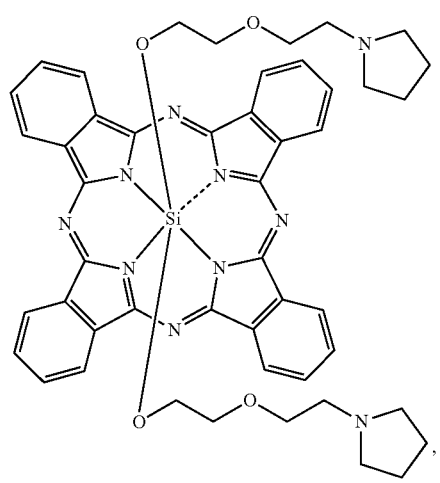
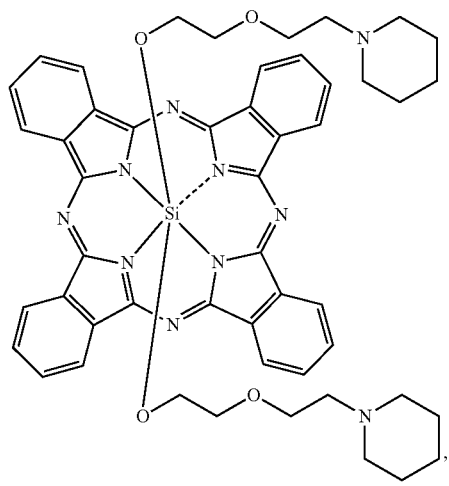
78
-continued
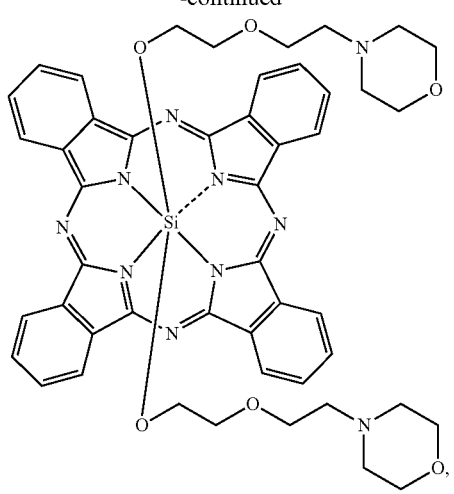
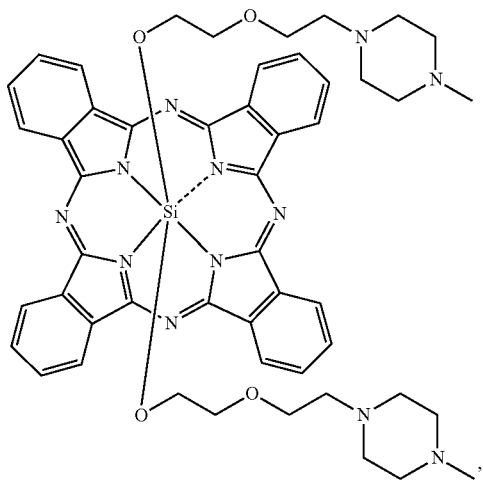
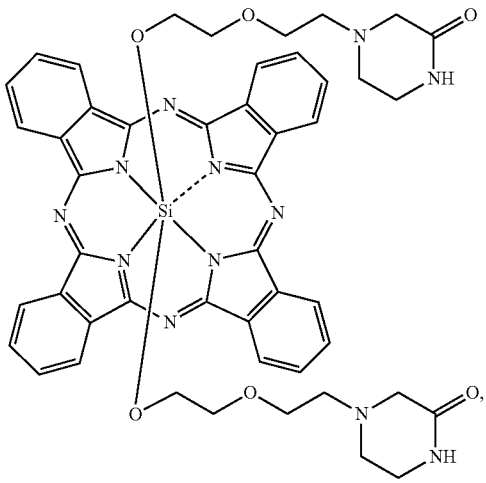

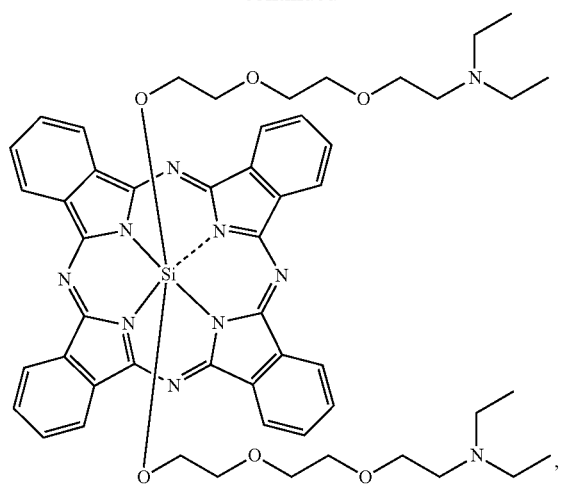
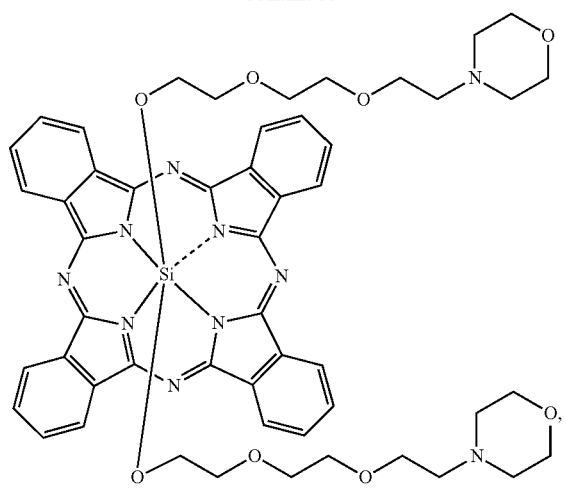
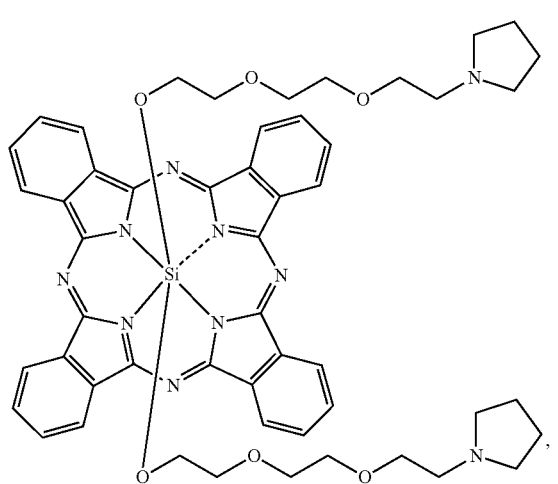
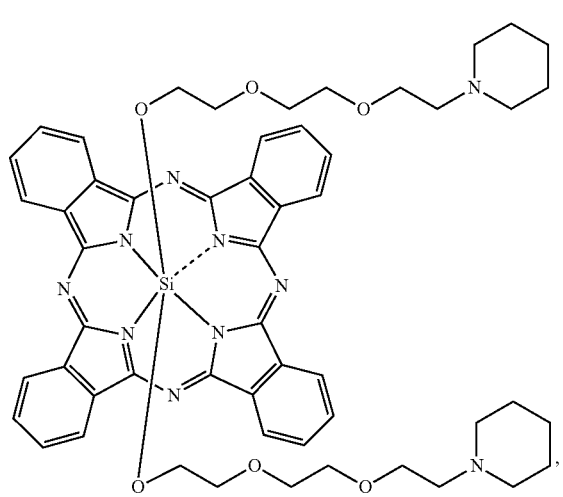
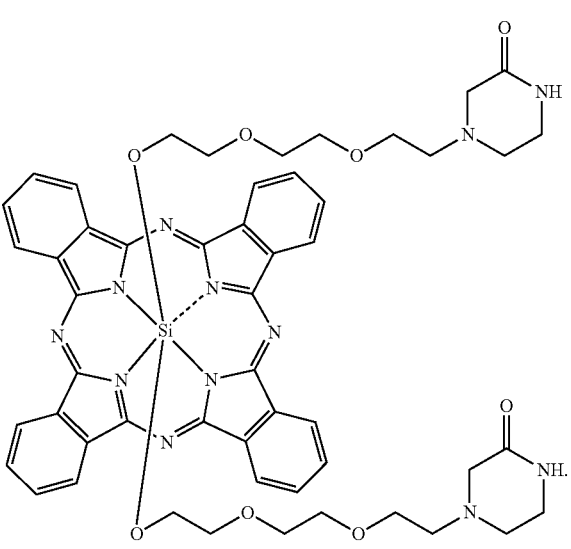
and

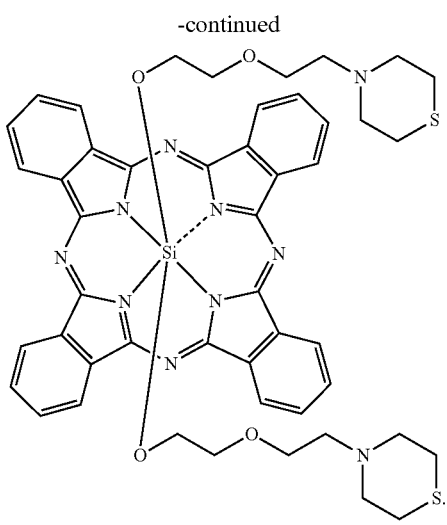

8. A process for preparing the compound of formula (I) according to claims 1 or 2, comprising a step of:

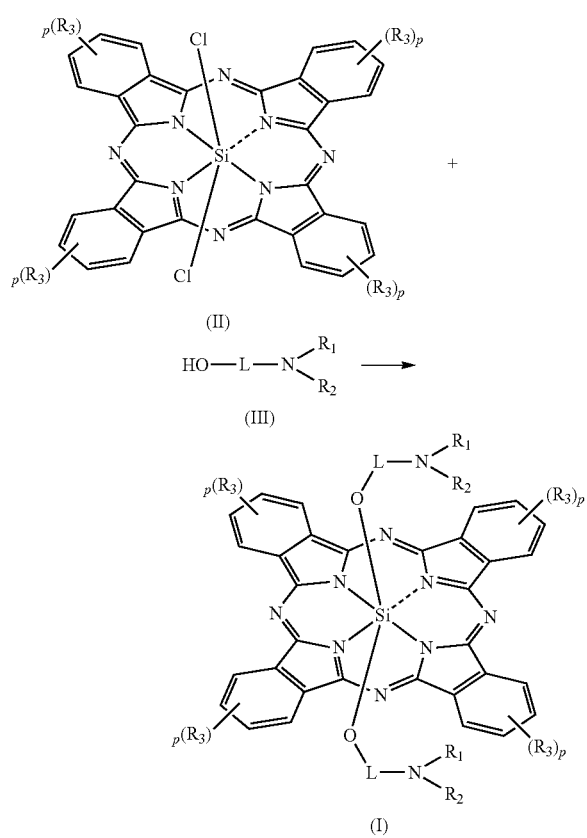

reacting a compound of formula (II) with a compound of formula (III) in an organic solvent under an alkaline condition to obtain the compound of formula (I);

wherein L, $R_1$-$R_3$ and p are as defined in claims 1 or 2.

9. The method according to claim 8, wherein:

the molar ratio of the compound of formula (II) to the compound of formula (III) is 1: 1-4, preferably 1: 2-3;

said organic solvent is selected from the group consisting of toluene, benzene, xylene, hexane, N,N-dimethylformamide, dimethylsulfoxide, ethyl acetate and acetone, preferably toluene;

said alkaline condition are provided by a reagent selected from the group consisting of pyridine, sodium hydride, triethylamine, N,N-diisopropylethylamine, 4-dimethylaminopyridine, potassium carbonate and sodium carbonate, preferably from pyridine or sodium hydride;

said reaction is carried out at a temperature of 0-200° C., preferably 20° C.-140° C.

10. A pharmaceutical composition, comprising a therapeutically effective amount of the compound of formula (I) according to claim 1 and a pharmaceutically acceptable carrier, diluent or excipient.

11. A method for performing photodynamic or photosensitive therapy comprising the steps of administering the compound of formula (I) according to claims 1 or 2 or a pharmaceutical composition comprising the compound of claims 1 or 2 to a subject in need thereof, and irradiating the area to be treated with electromagnetic radiation.

12. A method for treating cancer comprising the steps of administering the compound of formula (I) according to claims 1 or 2 or a pharmaceutical composition comprising the compound of claims 1 or 2 to a subject in need thereof, and irradiating the area to be treated with electromagnetic radiation.

13. The method of claim 12, wherein said cancers are selected from the group consisting of skin cancer, esophageal cancer, lung cancer, brain tumor, head and neck cancer, eye tumor, inflammatory carcinoma, breast cancer, bladder cancer, rectal cancer, liver cancer, bile duct cancer, stomach cancer and ovarian cancer, preferably skin cancer and esophageal cancer.

* * * * *